(12) United States Patent
Polliack

(10) Patent No.: US 11,857,802 B2
(45) Date of Patent: Jan. 2, 2024

(54) INTRA-ORAL DEVICE FOR PROTECTING ORAL TISSUES DURING RADIATION TREATMENT

(71) Applicant: Grayduck Stents, LLC, Seattle, WA (US)

(72) Inventor: Adrian Polliack, Lake Oswego, OR (US)

(73) Assignee: GrayDuck Stents, LLC, Seattle, WA (US)

( * ) Notice: Subject to any disclaimer, the term of this patent is extended or adjusted under 35 U.S.C. 154(b) by 474 days.

(21) Appl. No.: 16/763,509

(22) PCT Filed: Nov. 13, 2018

(86) PCT No.: PCT/US2018/060864
§ 371 (c)(1),
(2) Date: May 12, 2020

(87) PCT Pub. No.: WO2019/094985
PCT Pub. Date: May 16, 2019

(65) Prior Publication Data
US 2020/0316401 A1    Oct. 8, 2020

Related U.S. Application Data

(60) Provisional application No. 62/585,505, filed on Nov. 13, 2017.

(51) Int. Cl.
*A61N 5/10*     (2006.01)
*A61B 13/00*    (2006.01)
*A61B 90/00*    (2016.01)

(52) U.S. Cl.
CPC ................ *A61N 5/10* (2013.01); *A61B 13/00* (2013.01); *A61B 90/04* (2016.02);
(Continued)

(58) Field of Classification Search
CPC .............. A61N 5/10; A61N 2005/1094; A61N 2005/1097; A61B 13/00; A61B 90/04;
(Continued)

(56) References Cited

U.S. PATENT DOCUMENTS 2,505,056 A * 4/1950 Terre ..................... A61B 1/24
                                                    600/24
2,588,169 A * 3/1952 Shea .................... A61C 9/0006
                                                    433/140

(Continued)

FOREIGN PATENT DOCUMENTS

WO   WO-2017064182 A1 *  4/2017
WO   WO-2017192676 A1 * 11/2017 ............. A61B 13/00

*Primary Examiner* — Thaddeus B Cox
*Assistant Examiner* — Marc D. Honrath
(74) *Attorney, Agent, or Firm* — Schaffer IP Law, LLC

(57) ABSTRACT

An intra-oral device for positioning oral tissues during medical treatment, for example, radiation treatment. The device includes upper and lower dental arch members configured to engage the maxillary and mandibular teeth or edentulous arch(es) of a patient, respectively. Moldable material is maintained within channels formed in the dental arch members by partially extruding the material through keyways formed in the arch members during the bite mold process. The upper and lower dental arch members are operatively coupled to provide a dental arch assembly. A protective element to displace or depress a patients tongue is secured at a suitable working position with respect to the dental arch assembly via a threaded strut adjustably coupled between the protective element and a support structure disposed between the dental arch members.

14 Claims, 14 Drawing Sheets

(52) U.S. Cl.
CPC .......... *A61B 2090/0436* (2016.02); *A61B 2090/0481* (2016.02); *A61N 2005/1094* (2013.01); *A61N 2005/1097* (2013.01)

(58) Field of Classification Search
CPC .... A61B 2090/0436; A61B 2090/0481; A61B 6/107; A61C 5/90
See application file for complete search history.

(56) References Cited

U.S. PATENT DOCUMENTS

| | | | | |
|---|---|---|---|---|
| 5,588,836 | A * | 12/1996 | Landis | A61C 17/08 433/93 |
| 2003/0024532 | A1* | 2/2003 | Sniadach | A61B 13/00 128/205.13 |
| 2013/0131427 | A1* | 5/2013 | Johnson | A61N 5/1014 600/1 |
| 2013/0209964 | A1* | 8/2013 | Nemeh | A61C 19/063 264/16 |
| 2015/0010879 | A1* | 1/2015 | Kurthy | A61C 3/02 433/214 |
| 2015/0230970 | A1* | 8/2015 | Kaner | A61F 5/566 128/848 |

* cited by examiner

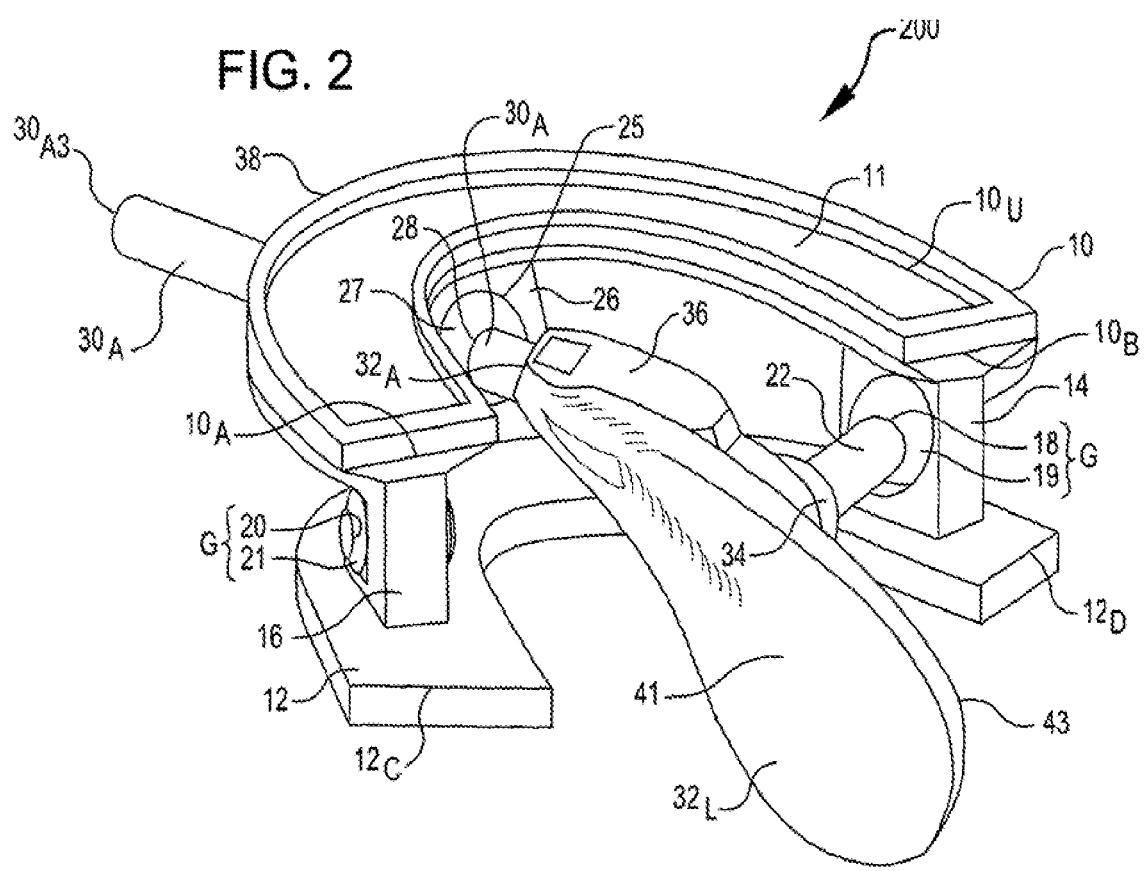
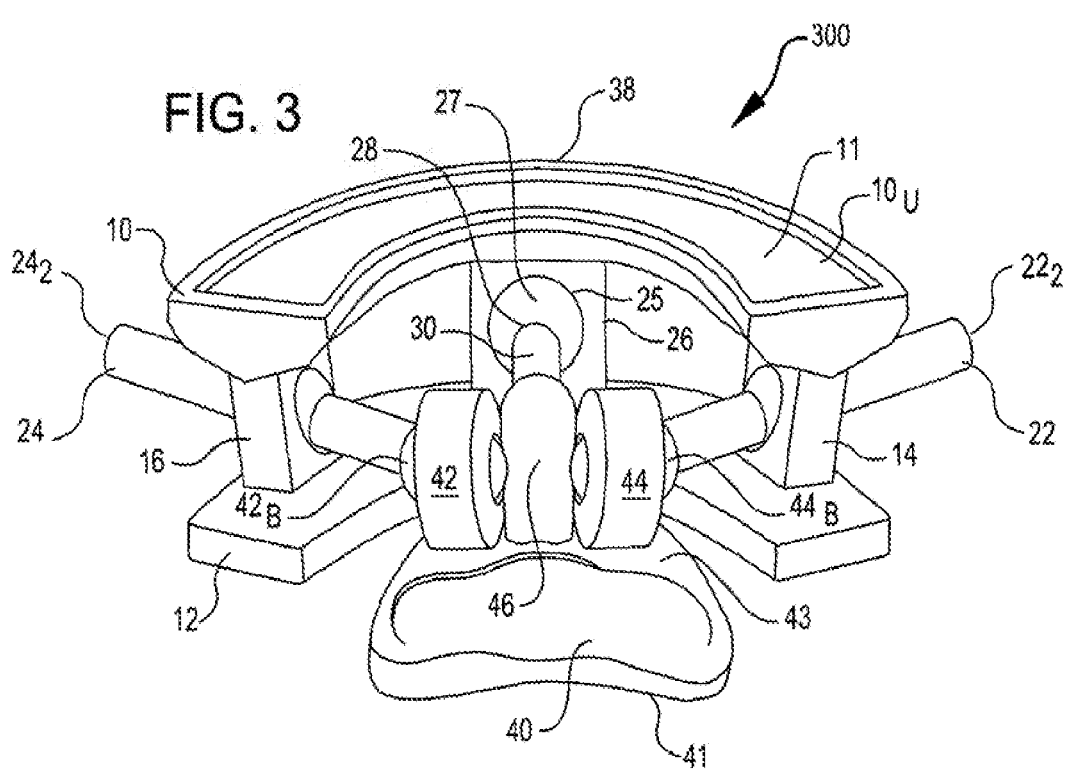

FIG. 16A  FIG. 16B  FIG. 16C  FIG. 16D
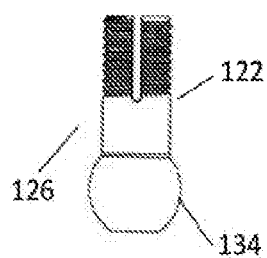
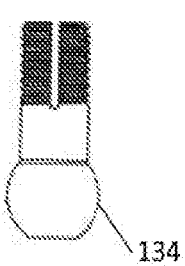
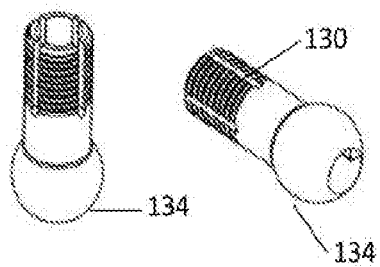
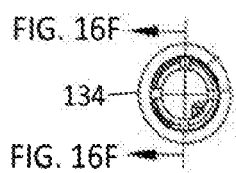
FIG. 16E
FIG. 16F
FIG. 16G
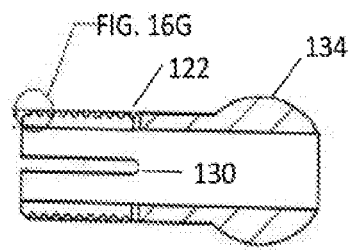

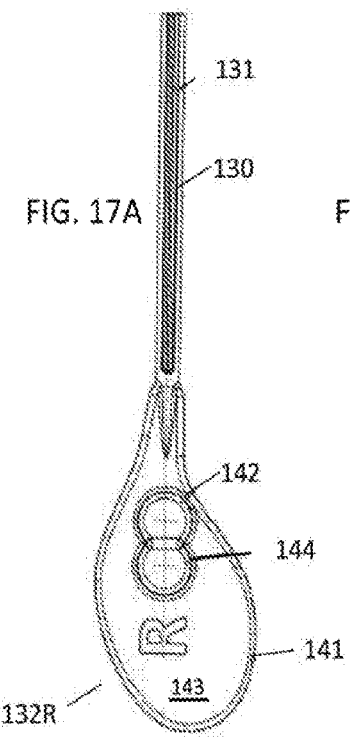
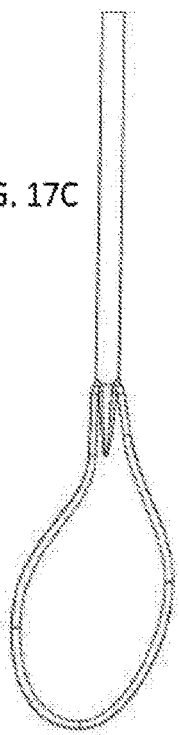
FIG. 17A   FIG. 17B   FIG. 17C   FIG. 17D
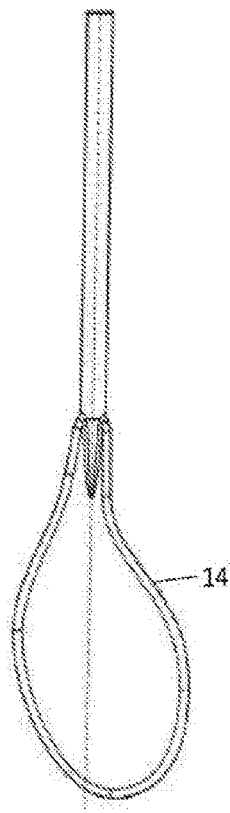
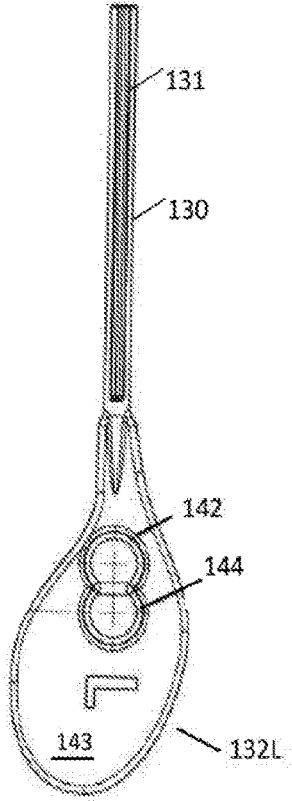
FIG. 18A   FIG. 18B   FIG. 18C   FIG. 18D

INTRA-ORAL DEVICE FOR PROTECTING ORAL TISSUES DURING RADIATION TREATMENT

1. CROSS-REFERENCES TO RELATED APPLICATIONS

This application claims the benefit of U.S. Provisional Patent Application No. 62/585,505, filed Nov. 13, 2017, whose contents are incorporated herein for all purposes.

BACKGROUND OF THE INVENTION

Field of the Invention

This application relates to devices for reducing exposure of certain tissues to ionizing radiation during treatment of head and neck cancers in patients, and to improved methods for use of such devices.

Description of the Prior Art

As is generally known, cancer treatment can be complex and invasive. In some cases, patients need to be subjected to high-dose radiation treatment in order to eradicate and prevent additional cancerous tissue growth. In cases of head and neck cancer, cancerous tissue growth is typically located on the floor of the mouth, cheek lining, tonsils, pharynx, the tongue, and/or lymph nodes. When radiation treatment is applied in cases of head and neck cancer, some damage often occurs to non-cancerous tissues that lie in the pathway of the beam treating the cancer. For example, a patient's tongue may not be invaded by a cancer when the cancer is in the tonsils, but the tongue may be damaged by ionizing radiation that passes through the tongue in order to treat the tonsillar tumor. Thus, it would be advantageous if non-cancerous tissue could be spared radiation damage by altering the beam path, and/or by moving such non-cancerous tissue physically out of the way of the radiation beam.

One such device used to mitigate exposure of a patient's tongue to ionizing radiation is described in U.S. Pat. No. 9,504,537. This intra-oral device comprises upper and lower dental arch members that a patient bites down upon and includes a paddle that extends through a front section of the arch members and into the interior of the mouth adjacent the tongue. The paddle may be moved laterally so as to push the tongue far to the right or left and out of the way of the beam of ionizing radiation. Although such a device has proven effective, it includes certain features that invite improvement.

One such feature in need of improvement is that the paddle is only loosely coupled to the dental arch via a stabilizing strut that is only slidingly received within a gimbal sandwiched between the dental arches. This type of coupling can cause slippage during use so that the tongue slides back into the path of the radiation beam. A more permanent stabilizing method is required that maintains or even improves the adjustability and precision of the paddle in relation to the dental arches.

Another such feature of the intra-oral device in need of improvement is that the moldable material used to fill the dental arch troughs, e.g. the material used to conform to the shape of the patient's upper and lower teeth, is glued in place. Using glue to adhere this moldable material has several disadvantages in radiation procedures. Accordingly, other methods for affixing the moldable material within the dental arch troughs without requiring glue or other adhesive is desired.

SUMMARY OF THE INVENTION

An intra-oral device for positioning oral tissues in a patient, with or without maxillary and/or mandibular teeth, comprises a dental arch assembly having an upper dental arch member with a first end and a second end. The upper dental arch member is configured for engagement with the maxillary teeth or edentulous arch of a patient. The oral device further includes a lower dental arch member having a third end and a fourth end, where the lower dental arch member is configured for engagement with the mandibular teeth or edentulous arch of the patient. Furthermore, complementary structures are arranged on the dental arches for press-fitting the upper and lower dental arch together. The device lastly includes a protective element comprising a protective portion and a connector portion, where the protective element is coupled to the dental arch assembly, and is configured to engage oral tissues of a patient. The connector portion includes a threaded rod adjustably engageable with a threaded structure disposed between the upper and lower dental arch member and ending with a ball joint captured within a depression formed on a surface of the protective element for rotational movement of the ball joint within the depression.

In a further aspect of the invention, the upper dental arch member further comprises an upper receiving trough with keyways formed therethrough, where the upper receiving trough and keyways are adapted to receive a moldable compound for fabrication into a bite pad for secure receipt of the occlusal surface of a patient's maxillary teeth or edentulous arch. The material is softened and pressure from the bite impression acts to force some of the material through the keyways. When the material within the keyways cures, the portion that mushrooms out the opposite portion of the keyway acts to lock the material within the trough.

BRIEF DESCRIPTION OF THE DRAWINGS

The foregoing figures, being merely exemplary, contain various elements that may be present or omitted from actual apparatus that may be constructed, or used to practice the methods taught herein, and to manufacture the intra-oral devices as set forth herein. An attempt has been made to draw the figures in a way that illustrates at least those elements that are significant for an understanding of the devices taught herein, and for the alternate configurations thereof, and for the methods of use of the devices. However, various other elements for such intra-oral devices, for the methods of use thereof, may be utilized, within the teachings hereof and within the coverage of the claims set forth herein.

Novel intra-oral devices will be described by way of exemplary embodiments, illustrated in the accompanying drawing figures in which like reference numerals denote like elements, and in which:

FIG. 2 is a perspective view of an embodiment the intra-oral device in mirror image to that shown in FIG. 1.

FIG. 3 is a perspective view of an alternate embodiment for an intra-oral device to that shown in FIG. 1.

FIGS. 16A-G show different perspective, elevation, plan, section, and partial views of a threaded gimbal constructed according to teachings of the invention for use within intra-oral devices described in the above FIGs.

FIGS. 17A-D show different elevation views of a right paddle used in combination with the intra-oral devices described in the above FIGs.

FIGS. 18A-D show different elevation views of a left paddle used in combination with the intra-oral devices described in the above FIGs.

DETAILED DESCRIPTION

Intra-oral devices for protecting head and neck tissues during radiation treatment, and method(s) for using such various embodiments of such devices, are described herein. FIGS. 1-10 illustrate various embodiments of the entirety of the intra-oral device with the remaining figures showing various improved aspects and features of the device.

Figure 1:
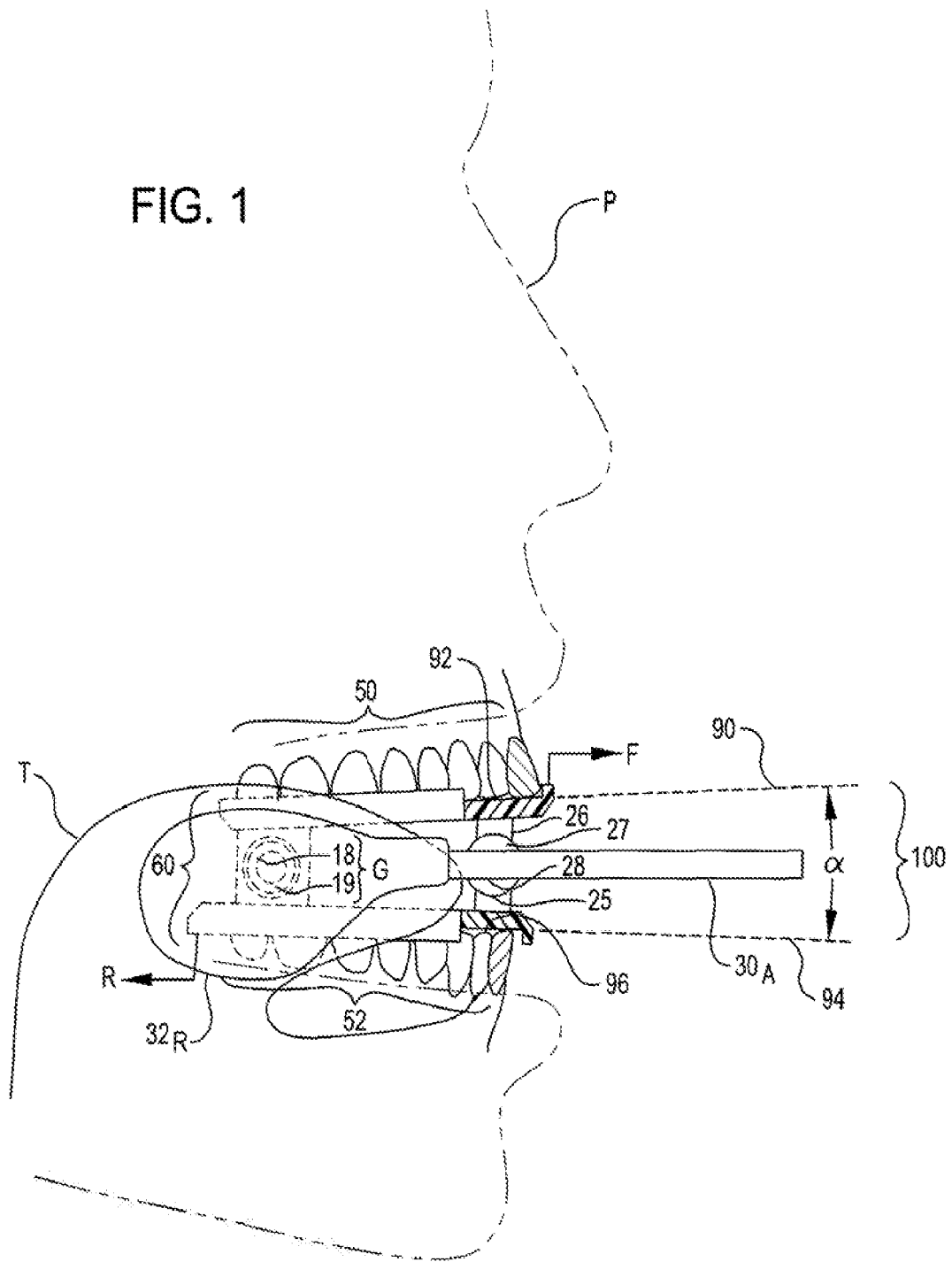
FIG. 1 illustrates a side-elevation view in partial section of the oral-device of a first embodiment of the invention positioned within the mouth of a patient.

FIG. 1 shows, during fitting of a patient for use, a partial cross-sectional view of an embodiment for an intra-oral device for protecting oral tissues during radiation treatment, showing upper and lower dental arch members, a tongue-deviating paddle, and showing a midline rod in location for moving the tongue-deviating paddle for suitable tongue position adjustment, whether by in/out, up/down, or left/right movement of the tongue-deviating paddle, as further described herein. In FIG. 1, an intra-oral device 100 is shown being fitted to a patient P for movement of the patient's tongue T, which may be envisaged from the illustration to be, in an embodiment, to the patient's right.

FIG. 2 shows upper and lower dental arch members, a left tongue-deviating paddle, and a midline rod in location for moving the left tongue-deviating paddle for suitable tongue position adjustment, whether by in/out, up/down, or left/right movement of the left tongue-deviating paddle, and the use of a posterior stabilizing rod, all as further described herein below. In FIG. 2, a substantially mirror image configuration to intra-oral device 100 just noted above is provided in the form of an intra-oral device 200; the intra-oral device 200 is configured for movement of a patient P's tongue T to the left.

FIG. 3 is a rearward perspective view of an embodiment for an intra-oral device, showing upper and lower dental arch members, a tongue-depressing paddle, and showing a midline rod in location for moving the tongue-depressing paddle for suitable tongue position adjustment, whether by in/out, up/down, clockwise/counterclockwise rolling movement, or left/right movement of the tongue-depressing paddle, and the use of first and second posterior stabilizing rods, each of which may, in an embodiment, be moved in/out, up/down, or left/right, or rolled for suitable positioning of the tongue-depressing paddle. In FIG. 3, an intra-oral device 300 is depicted which is configured for guiding movement of a patient P's tongue T downward.

Figure 4:
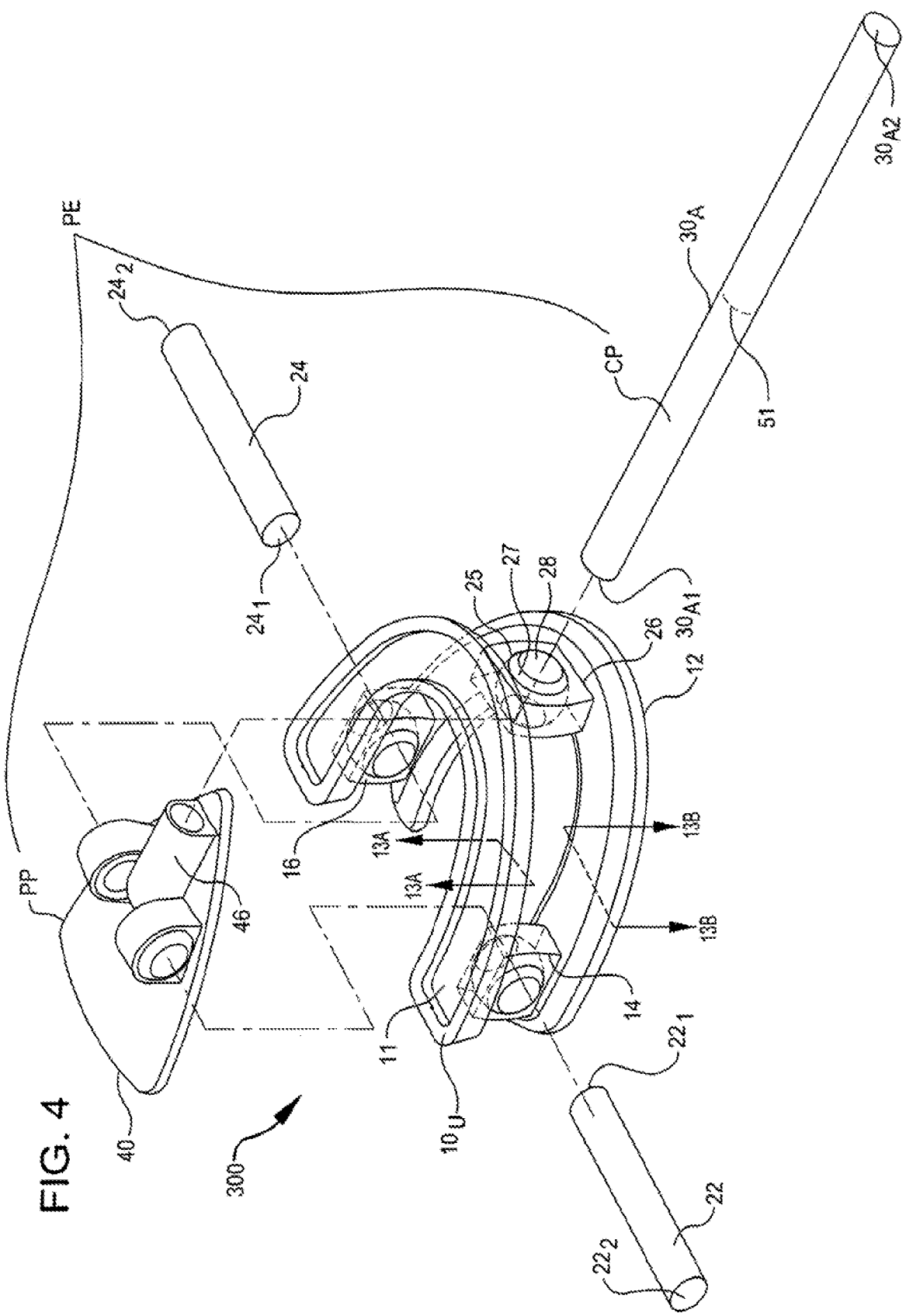
FIG. 4 is an exploded perspective view of an embodiment for an intra-oral device of FIG. 3.

FIG. 4 is an exploded perspective view of an embodiment for an intra-oral device of FIG. 3, showing upper and lower dental arch members which are joined to form a dental arch assembly, a tongue-depressing paddle, and showing a midline rod in location for assembly through an adjustable guide portion (that is, disposed so as to tie parts together in a manner that allows motion between the dental arch assembly and the tongue-depressing paddle) and attachment of the midline rod to the tongue-depressing paddle for suitable tongue position adjustment, whether by in/out, up/down, or left/right movement of the tongue-depressing paddle, and the provision of first and second posterior stabilizing rods in location for assembly in each case through an adjustable guide portion and attachment to a left side and a right side of the tongue-depressing paddle, respectively.

Figure 5:
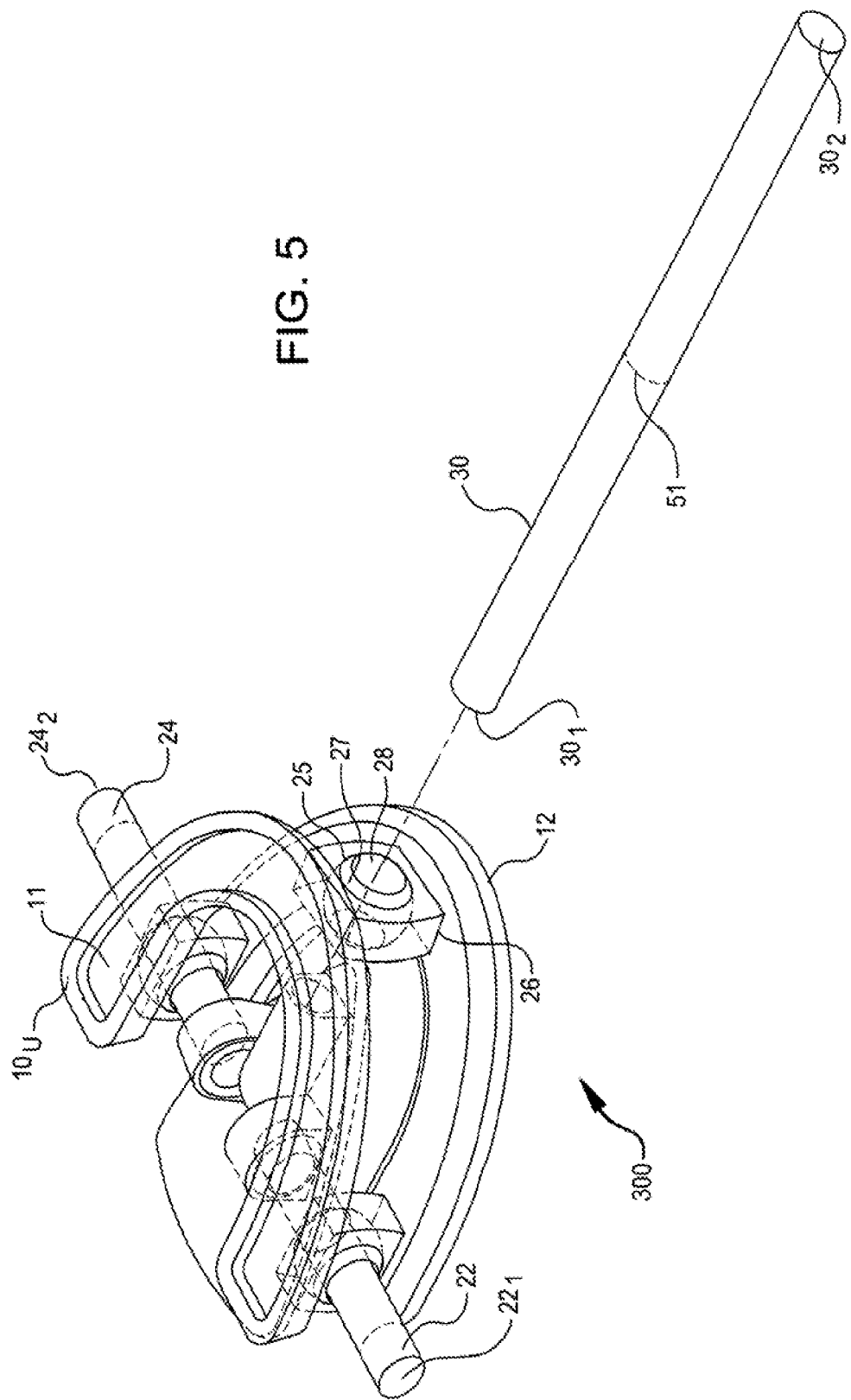
FIG. 5 is a partially assembled exploded perspective view of an embodiment for an intra-oral device, similar to that just shown in FIG. 4.

FIG. 5 is a partially assembled exploded perspective view of an embodiment for an intra-oral device, similar to that just shown in FIG. 4, showing upper and lower dental arch members which are joined to form a dental arch assembly, and now showing a tongue-depressing paddle in an initial position with first and second posterior stabilizing rods in location assembled through an adjustable guide portion and attached to a left side and a right side of the tongue-depressing paddle, respectively, and also showing a midline rod attachment of the midline rod yet to be inserted through an adjustable guide portion and affixed to a tongue-depressing paddle for suitable tongue position adjustment in a patient.

Figure 6:
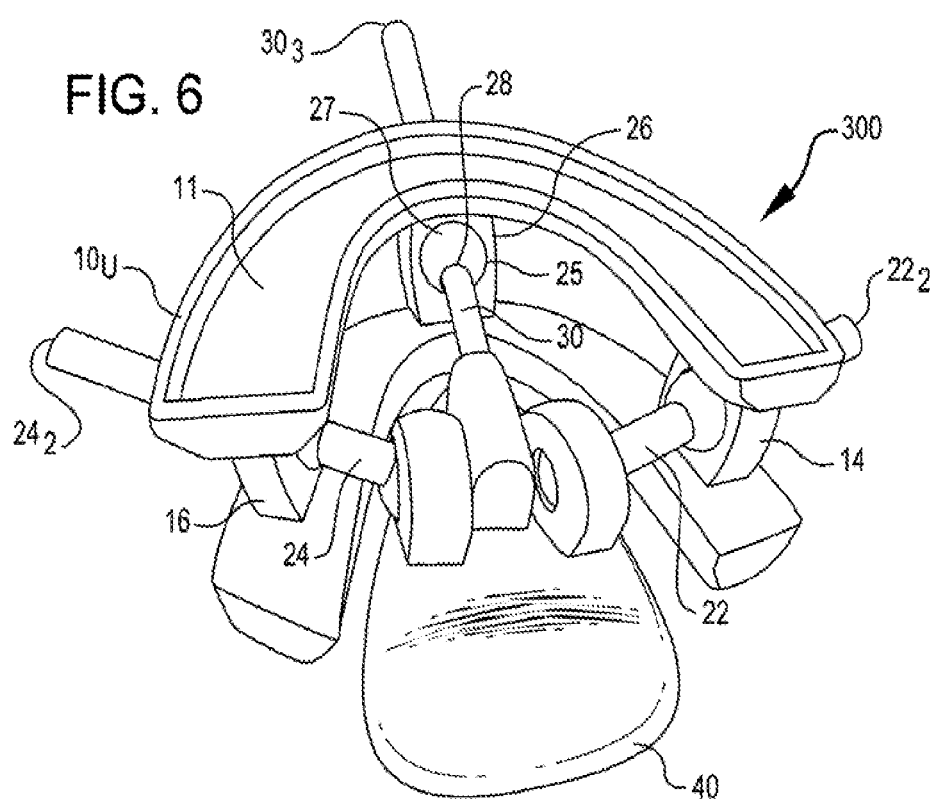
FIG. 6 is a perspective view taken looking down and from the rear at an embodiment of a fully assembled intra-oral device, similar to that just shown in FIGS. 4 and 5.

FIG. 6 is a perspective view taken looking down and from the rear at an embodiment of a fully assembled intra-oral device, similar to that just shown in FIGS. 4 and 5, showing upper and lower dental arch members which are joined to form a dental arch assembly, and now showing a tongue-depressing paddle in an initial position with first and second posterior stabilizing rods in location assembled each through an adjustable guide portion and attached to a left side and to a right side of a tongue-depressing paddle, respectively, and also showing a midline rod attachment of the midline rod inserted through an adjustable guide portion and affixed to a tongue-depressing paddle for suitable tongue position adjustment in a patient.

Figure 7:
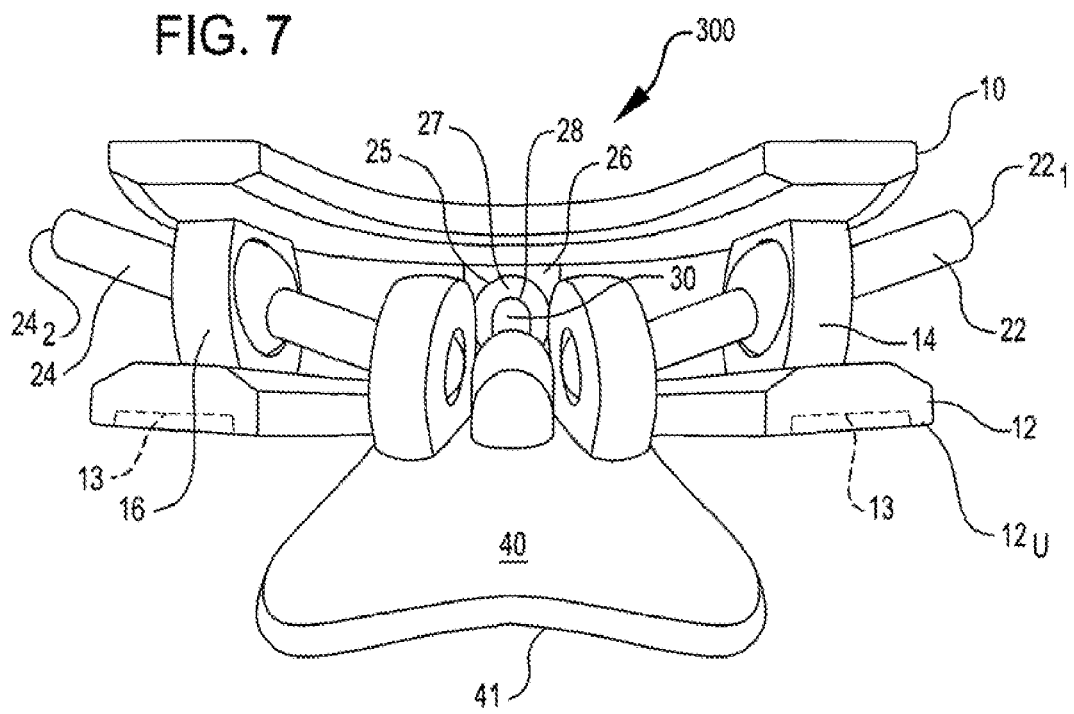
FIG. 7 is a side view taken looking from the rear at an embodiment of a fully assembled intra-oral device, similar to that just shown in FIGS. 4, 5, and 6.

FIG. 7 is a side view taken looking from the rear at an embodiment of a fully assembled intra-oral device, similar to that just shown in FIGS. 4, 5, and 6, here showing upper and lower dental arch members which are joined to form a dental arch assembly, and now showing a tongue-depressing paddle in an initial position with first and second posterior stabilizing rods in location assembled each through an adjustable guide portion and attached to a left side and to a right side of a tongue-depressing paddle, respectively, and also showing a midline rod attachment of the midline rod inserted through an adjustable guide portion and affixed to a tongue-depressing paddle for suitable tongue position adjustment in a patient, which in this view with the posterior stabilizing rods in a dihedral configuration wherein they slope downwardly from their respective adjustable guide portions at the dental arch assembly to their respective attachment points to the tongue-depressing paddle.

Figure 8:
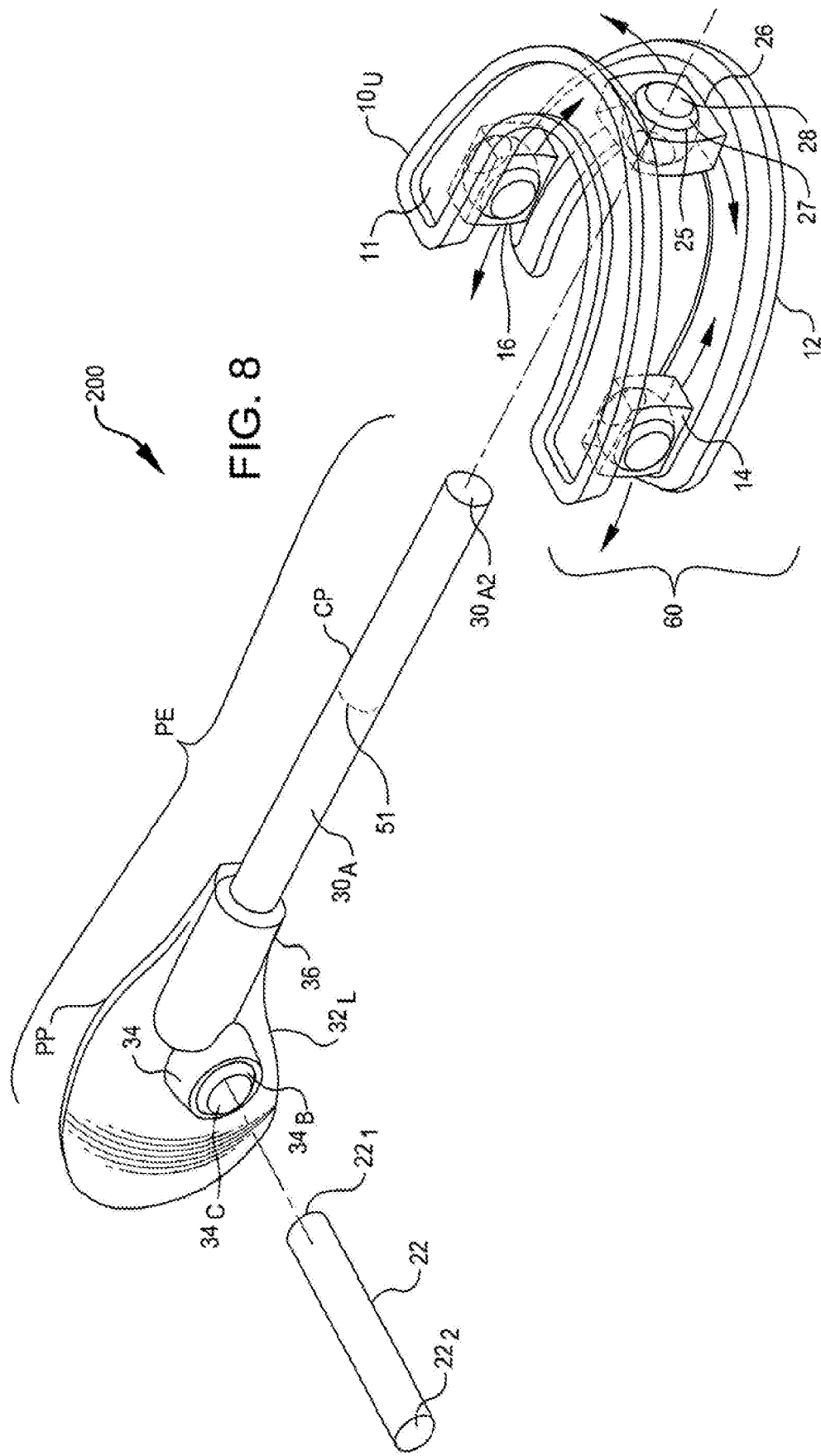
FIG. 8 is a partially exploded perspective view of an embodiment for an intra-oral device of FIG. 2.

FIG. 8 is a partially exploded perspective view of an embodiment for an intra-oral device, showing major components for attachment of a left tongue-displacing paddle to a dental arch assembly, illustrating the use of first or right side posterior stabilizing rod in location assembled through an adjustable guide portion and attached to the right side of the left tongue-displacing paddle, and also showing a midline rod attached to a front rod receiving receptacle in the left tongue-displacing paddle, and configured for insertion of the midline rod through an adjustable guide portion in the dental arch assembly.

Figure 9:
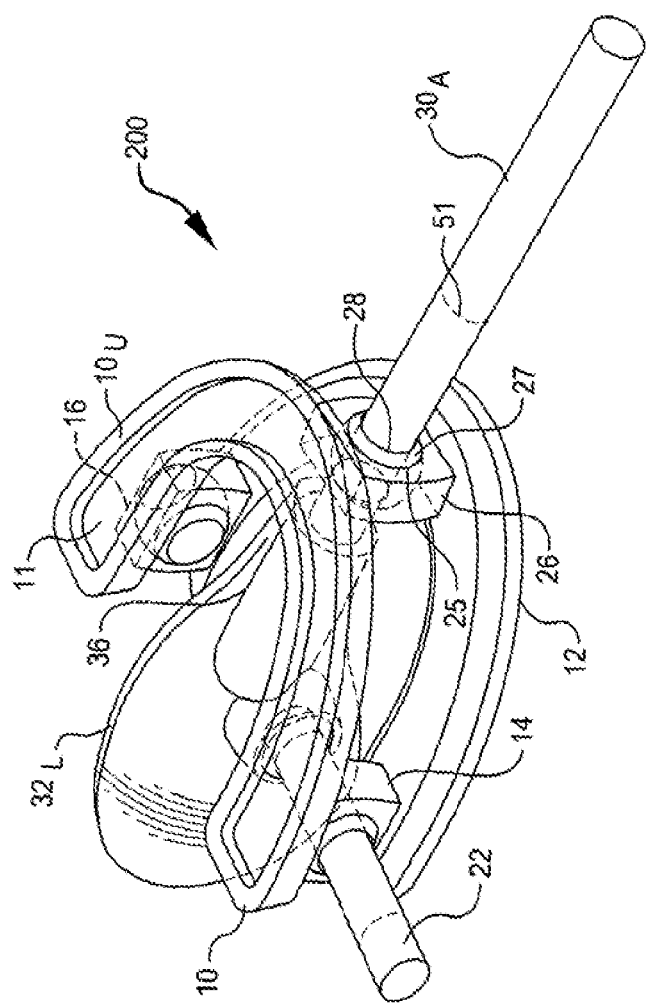
FIG. 9 is a perspective view of an embodiment for an intra-oral device of FIG. 2.

FIG. 9 is a perspective view of an embodiment for an intra-oral device, showing major components used in the attachment of a left tongue-displacing paddle to a dental arch assembly, illustrating the use of first or right side posterior stabilizing rod in location assembled through an adjustable guide portion and attached to the right side of the left tongue-displacing paddle, and also showing a midline rod attached to a front rod receiving receptacle in the left tongue-displacing paddle, and wherein the midline rod has been inserted through an adjustable guide portion in the dental arch assembly, and also noting a location in broken lines where the midline rod and posterior stabilizing rod may be shortened as desirable for convenient repeated use and/or for storage of the intra-oral device.

Figure 10:
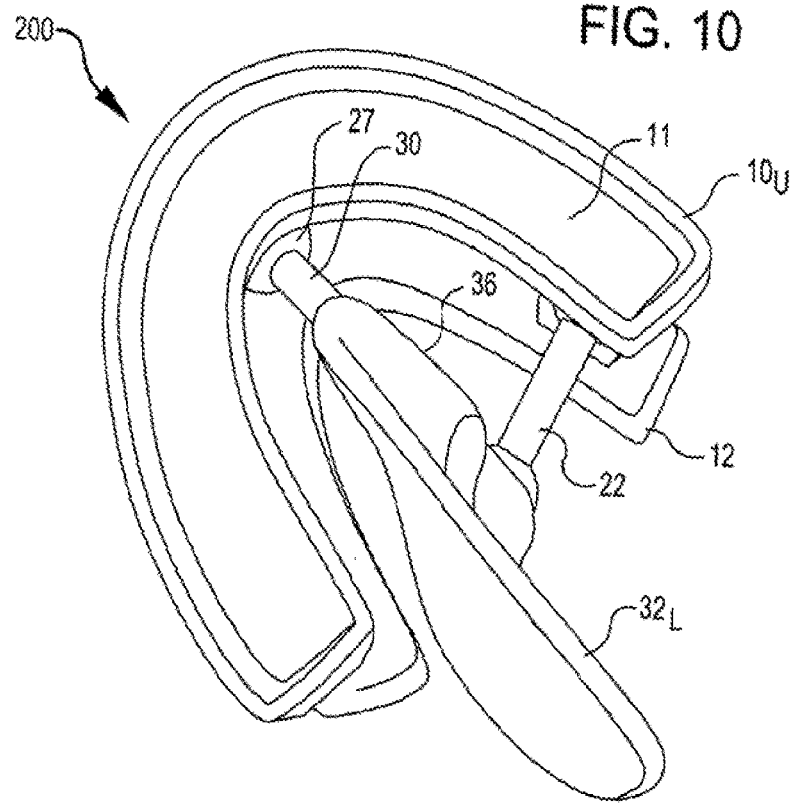
FIG. 10 is a top-down perspective view of an embodiment for an intra-oral device similar to that just shown in FIG. 9.

FIG. 10 is a perspective view of an embodiment for an intra-oral device similar to that just shown in FIG. 9, looking down at the intra-oral device, now showing major components used in the attachment of a left tongue-displacing paddle to a dental arch assembly, illustrating the use of first or right side posterior stabilizing rod in location assembled through an adjustable guide portion and attached to the right side of the left tongue-displacing paddle, and also showing a midline rod attached to a front rod receiving receptacle in the left tongue-displacing paddle, and wherein the midline rod has been inserted through an adjustable guide portion in the dental arch assembly, and also illustrating that for a given patient, the midline rod and posterior stabilizing rod each can be shortened for convenient repeated use and/or for storage of the intra-oral device.

Figure 11:
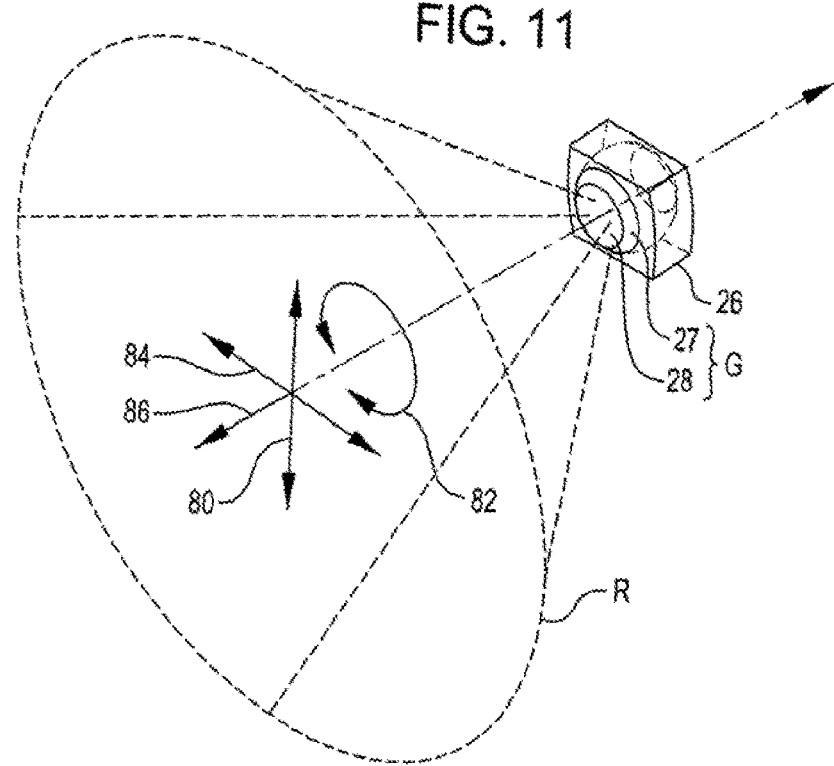
FIG. 11 is a perspective view of an embodiment for an adjustable guide portion that may be used in an embodiment for an intra-oral device.

FIG. 11 is a perspective view of an embodiment for an adjustable guide portion that may be used in an embodiment for an intra-oral device, a ball-type joint with range of motion to a limit of the freedom of movement of the joint (here the outer broken line circle), as, for example, may be provided in a spherical bearing within a housing and, in an embodiment further including a sleeve with fastener for securing a rod passing through it which provides freedom to alter the selected location for a rod as regards translation along the rod's longitudinal axis (i.e. in-out movement along the rod), and further illustrating a rod located in the adjustable guide (either during an adjustment or fitting phase, or after being secured, longitudinally) may be adjusted in a pitch axis motion (tongue deviating paddle moves up/down), or along a yaw axis motion (tongue deviating paddle moves left/right), or along a roll axis motion (top and bottom of the rod, and of the tongue deviating paddle, move in opposite directions as they are rolled).

Such intra-oral devices 100, or 200, or 300, or similar embodiments using the teachings hereof, may be useful in the reduction of damage to non-cancerous tissues of an oral cancer patient during radiation treatment. The intra-oral devices 100 or 200 provide structures such as tongue deviation paddle 32R (for movement of a patient's tongue to the right), or tongue deviation paddle 32L (for movement of a patient's tongue to the left) either of which can move a patient's tongue out of the way of a radiation beam during treatment. The intra-oral device 300 may include a tongue-depressing paddle 40 which may be used to depress a patient P's tongue T out of the way of a radiation beam during treatment. Structures such as tongue-deviation paddles 32L or 32R (which generally may be referenced herein without regard to "handedness" as tongue-deviation paddle 32) or a tongue-depressing paddle 40, may also hold a patient's tongue T or other adjacent tissues steady in a repeatable position so that a multi-dose radiation beam can be better targeted. Use of such intra-oral devices minimizes exposure and resulting damage from radiation to adjacent non-cancerous tissues. In various embodiments, and in methods of use thereof, intra-oral devices 100, or 200, or 300, or other embodiments and configurations described herein, may be configured to protect a patient's healthy tongue from the negative effects of radiation. In other embodiments, and methods of use thereof, intra-oral devices 100, or 200, or 300, or other embodiments and configurations made possible by the descriptions herein, may be configured to stabilize a cancerous lesion on a patient's tongue so that a radiation beam will have a relatively fixed, stable target volume during radiation treatment.

As just mentioned above, one component useful in an embodiment of intra-oral devices 100 or 200 which provides tongue-deviating functionality is a tongue-deviating paddle 32R or 32L. Such a tongue-deviating paddle 32R or 32L may be disposed in a roughly vertical configuration, such as depicted in FIGS. 1 and 2. However, note that the tongue-deviating paddles need not be oriented roughly vertically, and may be rotated to any desired angle. As noted in FIG. 1, and elsewhere herein, a tongue-deviating paddle noted with reference numeral 32R may be configured for urging a tongue to a patient's right. For example, as noted in FIG. 2 and elsewhere herein, a tongue-deviating paddle noted with reference numeral 32L may be configured for urging a tongue to a patient's left. In an embodiment, one of the uses of a tongue-deviating paddle, whether 32R or 32L, is to move a patient's tongue away from a side of the patient's mouth that has a cancer to be treated by radiation. Various embodiments for an intra-oral device 100 or 200 may be configured such that the position of a tongue-deviating paddle 32R or 32L may be adjusted to allow for customizing the device 100 or 200 to the particular size and shape of the mouth and tongue of a particular patient.

Additionally, in an embodiment of an intra-oral device 100 or 200, a tongue-deviating paddle 32R or 32L may alternately be disposed substantially horizontally in order to depress, raise, or otherwise stabilize the patient's tongue. In such manner, the positioning of tongue-deviating paddle 32R or 32L may optionally also include support of a tongue toward one side or another of a patient's mouth. Thus, in an embodiment for an intra-oral device 100 or 200, a tongue-deviating paddle 32R or 32L may be disposed substantially horizontally, to upwardly lift a tongue, or to downwardly depress a tongue, in order to hold a patient's tongue away from a cancerous zone in the patient's mouth, so as to minimize or prevent exposure of a patient's tongue or other tissues to radiation.

Figure 14:
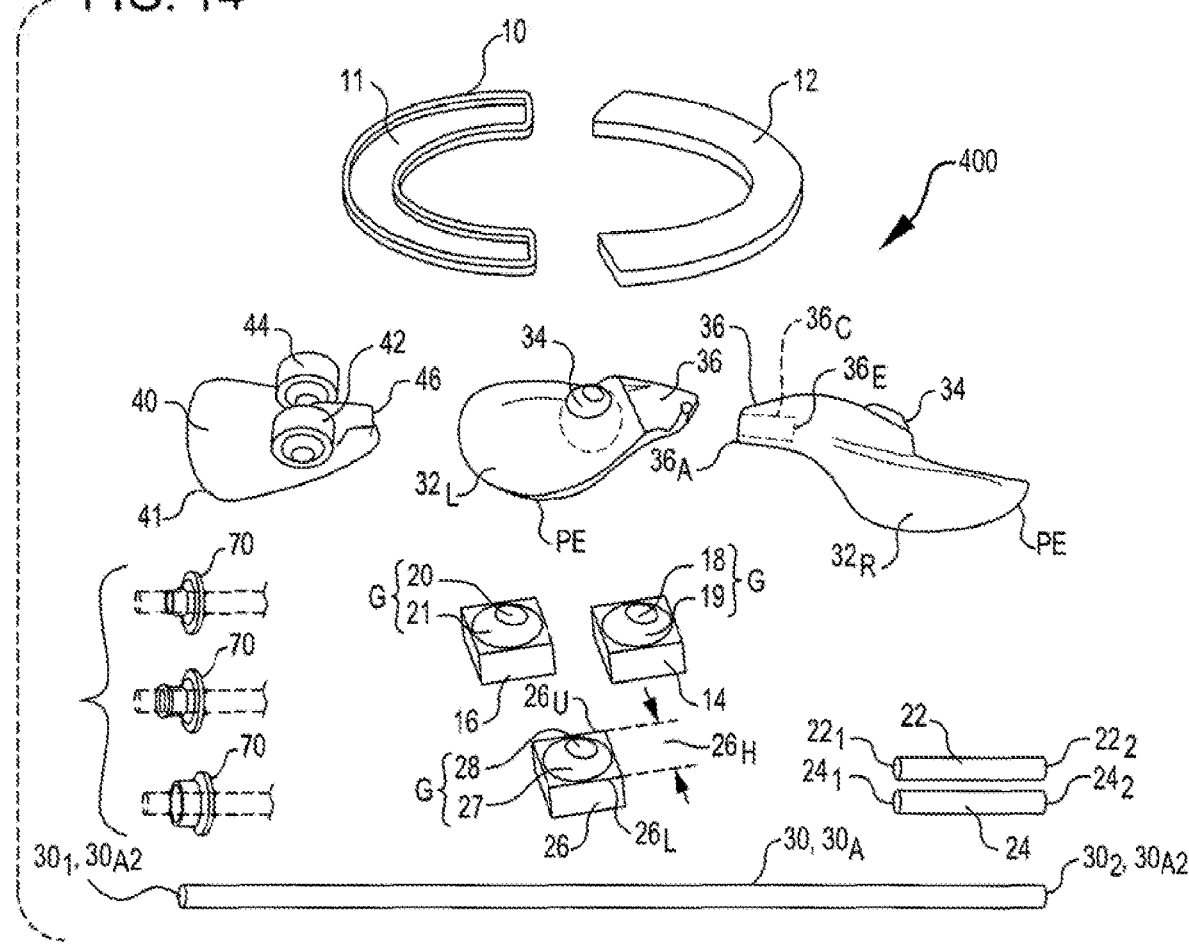
FIG. 14 illustrates an embodiment for a kit including various components that may be selected for assembly into an intra-oral device of FIGS. 1-3.

Intra-oral devices 100, 200, 300, or alternate embodiments according to the teachings hereof, may be provided in, or assembled from kits 400 as noted in FIG. 14, having components of various predetermined sizes. For example, small sized components, with small upper 10 and lower 12 dental arch members in a dental arch assembly 60 [FIG. 8], with small tongue-deviating paddles 32L and 32R and a small tongue-depressing paddle 40 may be provided. In another embodiment, medium sized components may be provided, with medium sized upper 10 and lower 12 dental arch members in a dental arch assembly 60, and medium sized tongue-deviating and/or medium size tongue-depressing paddles. In other embodiments, large sized components may be provided, having large upper 10 and lower 12 dental arch members in a dental arch assembly 60, and large tongue-deviating 32 and/or tongue-depressing paddles 40, all of which may be adapted for different sizes and shapes of mouths encountered in various patients P to be treated. Yet further, embodiments may be configured in a mix-match combination, mixing large, medium, or small components, to accommodate unusual mouth sizes or treatment environments as may be encountered in various patients. As depicted in FIG. 14, a kit 400 for fabrication of an intra-oral device 100, or 200, or 300 may include various components, and selected components may be assembled into an embodiment having primarily tongue-deviating functionality, or into an embodiment having primarily tongue-depressing functionality.

Attention is directed to FIG. 3, which shows an intra-oral device 300 having a tongue-depressing function, using a tongue-depressing paddle 40. The purpose of the tongue-depressing paddle 40 is to move a patient's tongue down, for example during treatment of a maxillary cancer, or to stabilize a patient's tongue in a secure position, for example during treatment of a mandibular or tongue cancer. The intra-oral device 300 may be configured such that the position of a tongue-depressing paddle 40 may be adjusted to allow for customizing to the particular size and shape of the mouth, and size and shape of a tongue, of a particular patient.

Figure 20A:
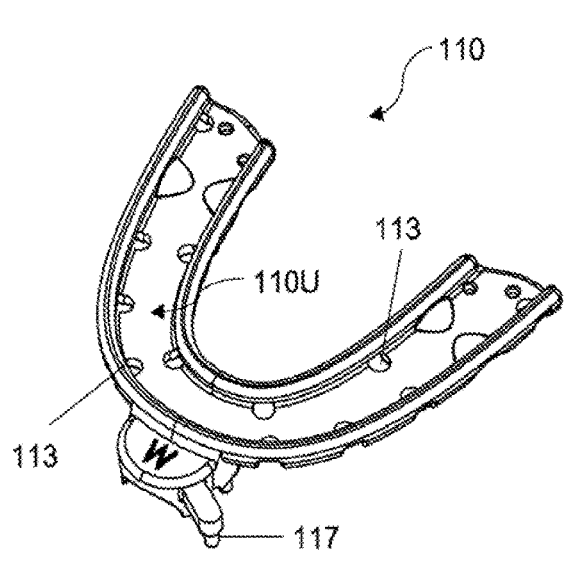
FIGS. 20A-B show top and bottom perspective views of upper trays of the intra-oral device constructed according to preferred embodiments of the invention.
Figure 20B:
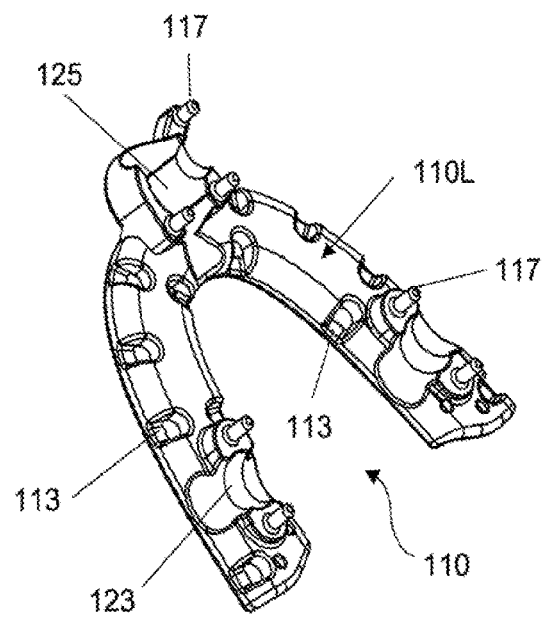

In various embodiments, an upper dental arch member 10 (or an improved upper dental arch 110 as shown in FIGS. 20A and 20B) may be separately provided. In a kit 400 (e.g., see FIG. 14), a selection of upper dental arch members 10 may be provided in preselected sizes, having a configuration complementary in size and shape to that of maxillary dental arch dimensions found in a selected group of anticipated patients. In an embodiment, an upper dental arch member 10 may be provided in a generally U-shaped (e.g., horseshoe shaped) configuration. An upper dental arch member 10 may be provided in various sizes, such as small, medium, large, or other sizes.

Figure 13A:
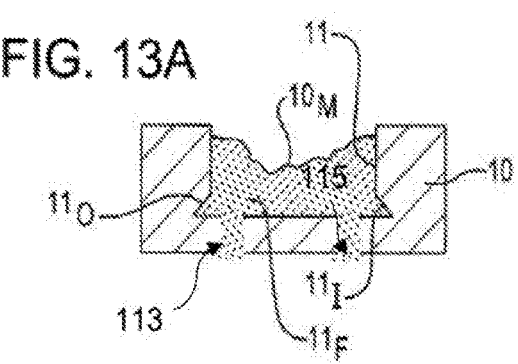
FIG. 13A is a cross section of an upper dental arch member with molded fill-in material, taken as at line 13A-13A of FIG. 4.
Figure 13C:
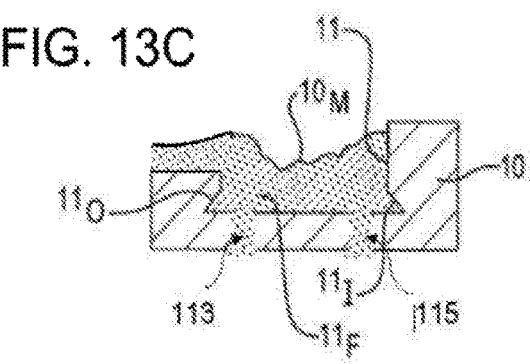
FIG. 13C is a cross section of an alternate version of the upper dental arch member having a wedge-shaped profile with molded fill-in material.

As may be appreciated from FIGS. 2, 3, 4 and 13A or 13C, in an embodiment, an upper dental arch member 10 may have an upper side 10U. An upwardly directed upper receiving trough 11 may be disposed on or in the upper side 10U. As seen in FIG. 13A, the upper receiving trough 11 may be adapted to receive a fill-in material 11F, which fill-in material 11F may be molded to customize the fit of the upper dental arch member 10 to an individual patient's maxillary teeth 50 (see FIG. 1) or edentulous maxillary arch. As seen in FIG. 13C, the upper receiving trough is shallower along an inner portion of the arch tray so as to form a wedge-shaped profile. A narrower (lower profile) inner portion of the stent (both the arch tray reduction and the insert profile reduction) assists with inserting the stent into the patient's mouth when the mouth opening is limited due to trismus, surgery or other reason. In a preferred embodiment, the inner portion of the insert is 160 mil lower in profile. The insert portion can also be thinner on the outer portion of the stent (by some 100 mil) to create a lower profile. The profile can be wedge-shaped, or stepped, or beveled so long as the inner wall portion is shallower than the outer portion. This combined with the inner portion profile reduction makes the stent easier to insert and form in a patient's mouth. Another key benefit of the different insert shapes is that the jaw opening as a result of the different profile thicknesses will mean that the medium stent (or larger of the two) opens the mouth approximately 2 cm, while the smaller design opens the jaw 1.5-1.7 cm. This is an additional feature.

The upper receiving trough may be variously adapted to receive a moldable compound for fabrication into a bite pad for secure receipt of the occlusal surface of a patient's maxillary teeth or edentulous arch. Optionally, as seen in FIG. 13A, in order to assist in the retention of the fill-in material 11F in the upper receiving trough 11, an inwardly directed wedge 111 and/or an outwardly shaped wedge 110 may be provided, such as by way of post molding machining of upper dental arch 10, or by using multipart fabrication techniques. Alternately, the fill-in material 11F may be retained as by using an array of keyways or apertures formed through the base or sidewalls of the trough 11 as shown in the embodiment of FIGS. 20A and 20B.

In various embodiments, a lower dental arch member 12 (or an improved lower dental arch 112 as shown in FIGS. 20A and 20B) may be provided. In a kit 400 (see FIG. 14), a selection of various sizes for a lower dental arch member 12 may be provided in a configuration complementary in size and shape to that of mandibular dental arch dimensions expected to be found in an anticipated patient population. In an embodiment, a lower dental arch member 12 may be provided in a generally U-shaped (e.g., horseshoe shaped) configuration. A lower dental arch member 12 may be provided in various sizes, such as small, medium, large, or other sizes.

Figure 13B:
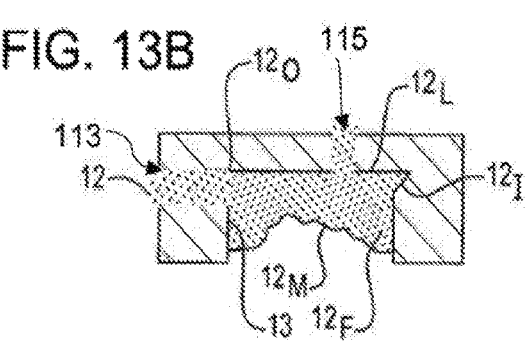
FIG. 13B is a cross section of a lower dental arch member with molded fill-in material, taken as at line 13B-13B of FIG. 4.

As may be appreciated from FIGS. 1, 7, and 13B, in an embodiment, a lower dental arch member 12 may have a lower side 12L on or in which a downwardly directed lower receiving trough 13 is provided. The downwardly directed receiving trough 13 may be adapted to receive a fill-in material 12F, which fill-in material 12F may be molded to customize the fit of the lower dental arch member 12 to an individual patient's mandibular teeth 52 (see FIG. 1) or edentulous mandibular arch.

Figure 13D:
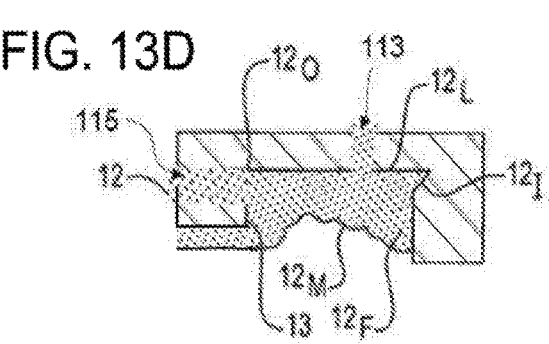
FIG. 13D is a cross section of an alternate version of the lower dental arch member having a wedge-shaped profile with molded fill-in material.

As seen in FIG. 13D, the lower receiving trough is shallower along an inner portion of the arch tray so as to form a wedge-shaped profile. A narrower (lower profile) inner portion of the stent (both the arch tray reduction and the insert profile reduction) assist with inserting the stent into the patient's mouth when mouth opening is limited due to trismus, surgery or other reason. In a preferred embodiment, the inner portion of the insert is 160 mil lower in profile. The insert portion can also be narrower on the outer portion of the stent (by some 100 mil) to create a lower profile. This combined with the inner portion profile reduction makes the stent easier to insert and form in a patient's mouth. Another key benefit of the different insert shapes is that the jaw opening as a result of the different profile thicknesses will mean that the medium stent (or larger of the two) opens the mouth approximately 2 cm, while the smaller design opens the jaw 1.5-1.7 cm. This is an additional feature. The advantage of the insert extending to sit on the walls of the arch tray (as with FIG. 13C) is to accommodate a wide range of jaw sizes. Without this design change, the insert that seats inside the walls of the arch tray, creates a greater likelihood that a smaller or larger mouth might have teeth rest on the arch tray lip/wall rather than the insert material.

Figure 21A:
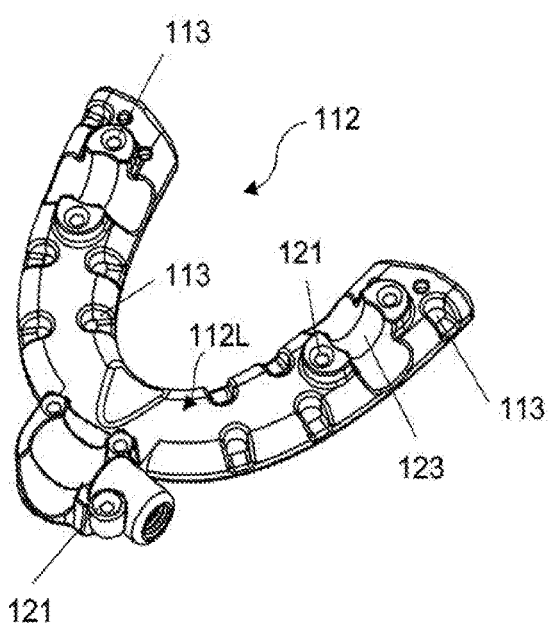
FIGS. 21A-B show top and bottom perspective views of lower trays of the intra-oral device constructed according to preferred embodiments of the invention.
Figure 21B:
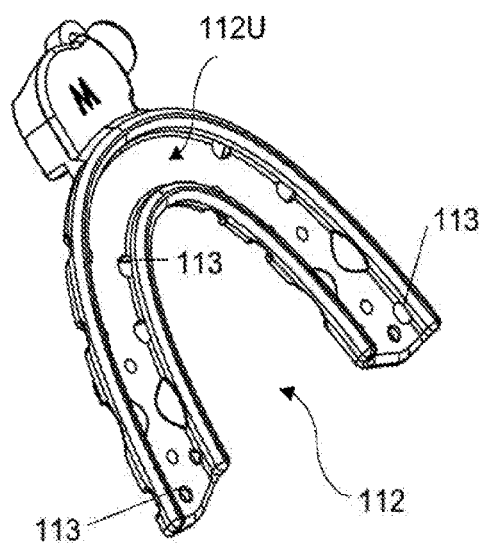

The lower receiving trough 13 may be variously adapted to receive a moldable compound for fabrication into a bite pad for secure receipt of the occlusal surface of a patient's mandibular teeth or edentulous arch. Optionally, as seen in FIG. 13B, in order to assist in the retention of the fill-in material 12F in the lower receiving trough 13, an inwardly directed wedge 121 and/or an outwardly shaped wedge 120 may be provided, such as by way of post molding machining of lower dental arch 12, or by using multipart fabrication techniques. Alternately, the fill-in material 11F may be retained as by using an array of keyways or apertures formed through the base or sidewalls of the trough 11 as shown in the embodiment of FIGS. 21A and 21B.

In various embodiments, the upper dental arch member 10 and the lower dental arch member 12 are joined together to provide a dental arch assembly 60. As seen in FIG. 2, in an embodiment, the upper dental arch member 10 may be connected to the lower dental arch member 12 by an anterior strut 26. In an embodiment, posterior struts 14 and 16 may connect the upper dental arch member 10 and lower dental arch member 12. As noted in FIG. 2, in an embodiment, upper dental arch member 10 may include a first end 10A and a second end 10B. In an embodiment, the lower dental arch member 12 may include a third end 12C and a fourth end 12D. The upper dental arch member 10 and the lower dental arch member 12 may be joined to each other at, near, or adjacent their respective posterior aspect (that is, the open end of their "U" shape). On one side, at, adjacent, or near first end 10A and third end 12C, upper member 10 and lower member 12 may be joined together. On an opposing side, at, adjacent, or near second end 10B and fourth end 12D, upper member 10 and lower member 12 may be joined together.

In an embodiment, as seen in FIGS. 2-9, struts 14 and 16 may allow anterior-posterior placement at selected locations between the upper dental arch member 10 and the lower dental arch member 12. Thus, the upper dental arch member 10 and the lower dental arch member 12 may be moved forward F or rearward R with respect to each other as noted by reference arrows in FIG. 1. In an embodiment, provision of adjustable struts 14 and 16 (for example, sliding or hinged components for attachment to one or both of the upper dental arch member 10 and lower dental arch member 12) may allow adjustment for a fabricating a dental arch assembly with regard to the amount of interincisal opening.

As seen in FIGS. 2 and 3, an embodiment, the struts 14 and 16 may include therein an adjustable guide G, which may be provided in the form of a spherical bearing or ball joint 19 and 21, respectively. Such ball joints 19 and 21 may have therein a through joint aperture such as a slot or hole defined by internal sidewall 18 or 20, respectively, which allow a tongue-deviating paddle 32 or tongue-depressing paddle 40 to be adjusted in a medial and/or lateral direction (that is, in a front to back or in a side to side fashion), an in various embodiments, in up and down directions as well.

In an embodiment, at time of fabrication the struts 14 and 16 may be adjustable so as to allow the fabricator to conform the upper dental arch member 10 and lower dental arch member 12 to a patient's jaw and/or tongue shapes, or treatment objectives. In such embodiment, at time of fabrication, the struts 14 and/or 16 may be moved forward or backward, so as to configure the upper dental arch member at a suitable location relative to the lower dental arch member.

Attention is now directed to FIG. 3, where posterior stabilizing rods 22 and 24 are shown. Rods 22 and 24 provide structural connector, for example between dental arch 60 and tongue-deviating paddle 32 or tongue-depressing paddle 40. Rods 22 and 24 may be sized and shaped to be inserted through the through joint aperture such as slots or holes defined by sidewalls 18 and/or 20 in the ball joints 19 and/or 21 of struts 14 and/or 16. As seen in FIG. 3, posterior stabilizing rods 22 and 24 may be utilized to locate and secure a tongue-depressing paddle 40. Alternately, as depicted in FIG. 2, a posterior stabilizing rod such as rod 22 may be utilized to locate and secure a tongue-deviating paddle 32.

As seen in FIG. 2, at the anterior aspect, that is, at the front 38 of the device, an anterior strut 26 may be attached to join the upper member 10 and the lower member 12 in such a way that the anterior strut 26 may be provided of selected height 26H between a lower side 26L placed at lower dental arch member 12, and an upper side 26U placed at upper dental arch member 10 (see FIG. 14), and thus can adjustment may be tolerated with respect to differences in the interincisal distance in various patients. An anterior strut 26 may also provide a housing 25 for a rotating spherical bearing or ball joint 27 that may have a running through it a guide hole or slot defined by interior sidewalls 28. The anterior strut 26 may be configured to support and serve as an attachment point as regards the anterior/posterior location of a tongue-deviating paddle 32 or a tongue-depressing paddle 40. The anterior strut 26 may also be configured to support and serve as an X, Y and Z axis placement locator for a tongue-deviating paddle 32 or a tongue-depressing paddle 40. For example, see FIG. 11, wherein a range of motion limit R for an exemplary adjustable guide G such as ball joint 27 in strut 26 is illustrated (functionality may be similar for adjustable guides G in struts 14 and 16). In an embodiment, a connector portion CP is sized and shaped for adjustable engagement with the adjustable guide G. In an embodiment, such adjustable guides G may allow adjustment along one or more of (a) a pitch axis 80, (b) roll axis 82, (c) yaw axis 84, and (d) a linear axis 86. As shown in FIG. 2, a midline rod 30 can be sized and shaped to be complementary to a slot or hole defined by sidewalls 28 in ball joint 27 of anterior strut 26, to connect, locate, and secure a tongue deviating paddle 32. Likewise, as seen in FIG. 3, a midline rod 30 may be provided sized and shaped complementary to through joint aperture slot or hole defined by sidewalls 28 in ball joint 27 of anterior strut 26, to connect, locate, and secure a tongue-depressing paddle 40.

In an embodiment, a tongue deviating paddle 32 may be provided in generally oval or tear-drop shaped configuration. However, any convenient figuration may be utilized, and the device shall in no way be considered to limited structures and uses to such shapes as may be suggested for an embodiment In an embodiment, a tongue-deviating paddle 32, or a tongue-depressing paddle 40, may be provided with a midline rod 30A that will fit through the anterior strut 26 and protrude outward from the front of the dental arch assembly 60 for control during the fitting and placement stage. As seen in FIG. 2, a tongue-deviating paddle 32 may have a working surface 41 that at least in part has a concave surface toward a patient's tongue T (see FIG. 1, not shown in FIG. 2.) The tongue-deviating paddle may also have a convex surface 43 on a non-working side, that is, a side away from a patient's tongue. Affixed to, or provided as a part of a tongue-deviating paddle 32, a mount 34 may be provided for securing thereto a posterior stabilizing rod 22. Such posterior stabilizing rod may, in an embodiment, be sized and shaped to fit through the appropriate guides in the form of through joint aperture slots or holes defined by sidewalls 18 (alternately, guides defined in the form of through joint aperture slots or holes defined by sidewalls 20) in one of one or more posterior struts, which are here shown as struts 14 and 16, in order to locate and secure tongue-deviating paddle 32, so as to hold the tongue toward the contra lateral (opposite) side. The tongue-deviating paddles 32 may take different forms and sizes (e.g., small, medium, or large) and be configured to deviate to the right or to deviate to the left of a patient, depending on the side of a patient's mouth where their cancer that requires treatment is located.

Figure 15A:
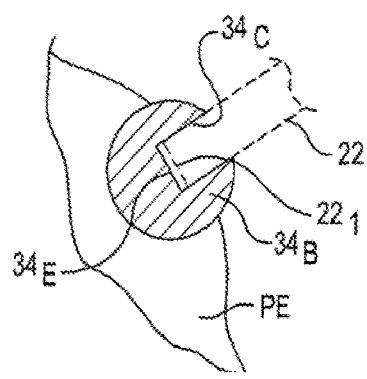
FIG. 15A is a cross section of a mount for use on a tongue-deviating paddle, including a spherical or ball joint that has a seat for a posterior stabilizing rod.

A tongue-deviating paddle 32 may be provided in a generally oval shaped or tear-drop-shaped tongue protection element PE having a mount 34 configured to receive at a first end 221 or 241 of one of the posterior stabilizing rods 22 or 24, respectively. In an embodiment, as may be appreciated by reference to FIG. 15A, mount 34 may be provided in the form of a seat formed in the protective element PE (e.g. tongue-deviating paddle 32) containing a spherical or ball type joint wherein ball 34B has a rod-receiving partial aperture defined by interior sidewalls wall 34C and interior end wall 34E.

In an embodiment, a protective element PE such as a tongue-deviating paddle 32 may further include a housing 36 that is sized and shape to receive a midline rod 30A. In an embodiment, the housing 36 may be defined by interior sidewalls 36C and by an end wall 36E, as noted in FIG. 14. In an embodiment, a housing 36 may be mounted at or near an anterior end 36A of a tongue-deviating paddle 32, and configured to receive a first end 30A1 of midline rod 30A.

Figure 15B:
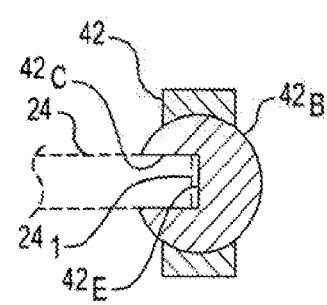
FIG. 15B is a cross section of a mount for use on a first side of a tongue-depressing paddle, including spherical or ball joint that has a seat for a posterior stabilizing rod.
Figure 15C:
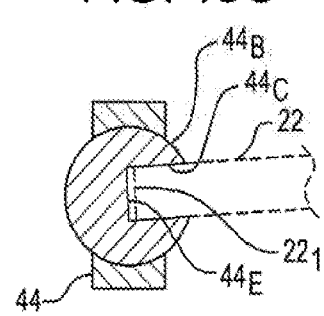
FIG. 15C is a cross section of a mount for use on a second side of a tongue-depressing paddle, including spherical or ball joint that has a seat for a posterior stabilizing rod.

As seen in FIGS. 3 and 7, a tongue-depressing paddle 40 may be provided with a tongue protection element 41. Such tongue protection element 41 may be provided in a generally oval-shape, or with a rounded triangular shape, or with a trapezoidal-shape, as suitable in particular circumstances. In an embodiment, joints 42 and/or 44 may be provided, and mounted on a first side 43 of the paddle 40. The joints 42 and/or 44 may be provided as ball mount joints, in that balls 42B and 44B, respectively, are provided with spherical freedom of movement in joints 42 and/or 44. In an embodiment, as noted in a cross-sectional view provided in FIGS. 15B and 15C, balls 42B and 44B may be provided with rod-receiving partial apertures defined by interior sidewalls walls 42C and 44C, and interior end walls 42E and 44E, respectively. The rod-receiving partial apertures defined by the just mentioned features are configured to receive and seat the posterior stabilizing rods 22 and 24, and more particularly a first end 221 or 241 of such rods, as noted in broken lines in FIGS. 15B and 15C. In an embodiment, the tongue-depressing paddle 40 may be provided with a housing 46 configured to receive the midline rod 30, which in an embodiment may be of the same configuration as described above as regards housing 36.

Embodiments of the intra-oral device 200 will now be further described with reference to FIGS. 2, 3 and 4. FIG. 2 illustrates an embodiment of an intra-oral device 200 configured with a tongue-deviating paddle 32. However, it must be understood that the tongue-deviating paddle 32 components and connecting parts as shown configured in FIG. 2 are interchangeable, and thus may be replaced by similar elements of different sizes, or of either right hand or of left hand configuration, and such alternate configuration will provide the tissue positioning functionality as described herein. As assembled, the intra-oral device 200 includes two elongate, essentially U-shaped members, namely an upper member 10 and a lower member 12. The upper member 10 and the lower member 12 are shown coupled together by struts 15 and 16.

Figure 12:
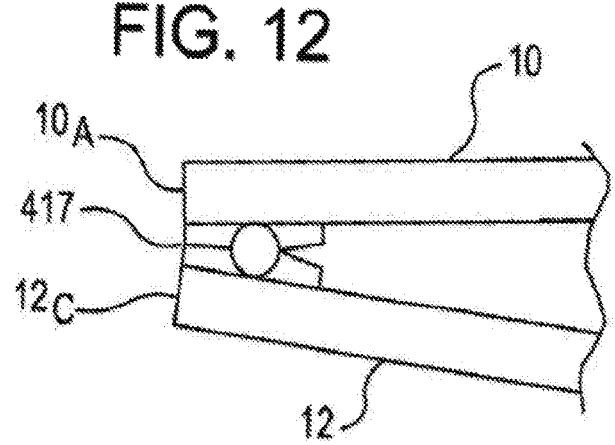
FIG. 12 provides a conceptual illustration of an optional coupling joint for joining an upper dental arch member (upper horseshoe) with a lower dental arch member to form a dental arch assembly.

As seen in FIG. 12, in another embodiment, an upper member 10 may be coupled to a lower member 12 using a moveable joint 417. Alternatively, upper member 10 and lower member 12 may be directly and fixedly attached together, as generally shown in FIGS. 2, 3, 6 and 8, for example.

FIG. 13A is a cross section of an upper dental arch member with molded fill-in material, taken as at line 13A-13A of FIG. 4, which configuration may be provided in an embodiment for an intra-oral device, showing an upper receiving trough (which may include slots or holes as shown in the improved dental arch embodiment shown in FIGS. 20A and 20B) in the upper dental arch member which may be filled with a fill-in material molded to fit a particular patient's teeth or edentulous arch(es). FIG. 13A illustrates a cross-section taken at line 13A-13A of FIG. 4 of an upper dental arch member 10. As shown in FIG. 13A, the upper dental arch member 10 may be provided with an upper receiving trough 11, which in an embodiment may generally be U-shaped. As noted above, the upper receiving trough 11 may be adapted to be filled with fill-in material 11F. The fill-in material 11F may be provided in the form of a moldable plastic or similar moldable material that may be cured once molded. Molded material may be provided responsive to the size and shape 10M of a patient's maxillary teeth 50, or edentulous arch, as suggested by illustrations provided in FIGS. 1, 4, and 13A.

FIG. 13B is a cross section of a lower dental arch member, taken as at line 13B-13B of FIG. 4, which configuration may be provided in an embodiment for an intra-oral device, showing a lower receiving trough (which may include slots or holes as shown in the improved dental arch embodiment shown in FIGS. 21A and 21B) in the lower dental arch member which may be filled with a fill-in material molded to fit a particular patient's teeth or edentulous arch(es). FIG. 13B illustrates a cross-section taken at line 13B-13B of FIG. 4 of a lower dental arch member 12. As shown in FIG. 13B, the lower dental arch member 12 may be provided with a lower receiving trough 13, which in an embodiment may generally be U-shaped. As noted above, the lower receiving trough 13 may be adapted to be filled with fill-in material 12F. The fill-in material 12F may be provided in the form of a moldable plastic or similar moldable material that may be cured once molded. A mold may be provided responsive to the size and shape of a patient's mandibular teeth 52, or edentulous arch, as suggested by illustrations provided in FIGS. 1, 4, and 13B.

When assembled an intra-oral device 200 may include an upper dental arch member 10 having upper molded surface 10M and a lower dental arch member 12 with lower molded surface 12M that as joined together, such as by struts 16 provide a dental arch assembly 60 which acts as an intermaxillary scaffold. The dental arch assembly 60 thus holds a patient's maxillary teeth/arch 50 and mandibular teeth/arch 52 (see, for example, the position of patient's teeth 50 and 52 and angle alpha α in FIG. 1) apart in a repeatable position in three-dimensional space, at a selected angle alpha α of opening, and, as may be possible with suitable patient tolerance consistent with medical objectives, at suitable forward or rearward positioning of the mandibular teeth/arch 52 in relation to the position of the maxillary teeth/arch 50.

In an embodiment, a dental arch assembly 60 should be considered to be an intra-oral device, even without the use of a protective element such as tongue deviating paddles 32 or tongue-depressing paddles 40 or the like. In any event, when a desired or prescribed opening position of a patient's mouth is achieved with the intermaxillary dental arch assembly 60 portion of the intra-oral device, 200, the device then additionally is used to provide supports for a protective element such as a "tongue paddle"—that is a tongue-deviating paddle 32R, 32L, or tongue-depressing paddle 40—and thus a selected paddle then displaces a patient's tongue in a prescribed direction and position.

After a dental arch assembly 60 is constructed, a protective element PE including protective portions PP (see FIG. 8) such as tongue paddle 32R or 32L may be inserted into a patient's mouth and loosely attached by way of an adjustable guide to the dental arch assembly 60. Using a posterior stabilizing rod 22 as a stabilizing device, rotating the tongue-deviating paddle 32L or 32R using midline rod 30A and the adjustable guide 27 as a fulcrum point, a patient's tongue may be positioned to a desired location. In an embodiment, once the patient's tongue T is in a suitable location, the anterior strut 26 and posterior strut 14 (or 16, as applicable) may be fixed to midline rod 30A and posterior stabilizing rod 22. In an embodiment, a locking mechanism 70 (e.g. compression fitting) may be utilized to fix in place any one or more of posterior stabilizing rods 22 or 24, or midline rods 30, or 30A (each of which is more fully described elsewhere herein). In an embodiment, fixation into a secure working position may be accomplished using a bonding agent, such as a curable bonding agent known in the field, such as light-cured acrylic, or by other methods such as by fusing the components with cyanoacrylate compositions or similar bonding agents. In any event, the objective is to assemble an intra-oral device, for example device 100, 200, or 300, into a secure configuration, and to lock the protective element such as a tongue-deviating paddle (e.g., 32L or 32R) or a tongue-depressing paddle 40 into a final, secure position. In various embodiments, such locking mechanisms may be irreversible (e.g., cyanoacrylate fusion) or reversible (mechanical locking mechanism 70).

One example of an improved mechanical locking mechanism is shown in FIGS. 16A-16G. The improved locking mechanism uses an anterior strut 126 having a ball joint 134 at one end and a threaded rod 122 extending therefrom. The threaded rod may have a length that is partially threaded as with the embodiment shown in FIGS. 16A-16E, or may be fully threaded along its length as with the rod 122 shown in FIGS. 19A and 19B. The threaded rod 122 may have four slots 130 spaced at 90 degrees about the barrel of the rod and formed at least partially along the length of the body of rod and such slots 130 allow the rod 122 to compress when fitted within a complementary gimbal to affect a greater friction fit within the gimbal as described further below.

Referring back to FIG. 2, the intra-oral device 200 may include an oval-shaped or tear-drop shaped tongue protective element, e.g., tongue-deviating paddle 32. In an embodiment, a paddle (e.g. 32 or 40) may be positioned in the middle of the device 200. In an embodiment, a tongue deviating paddle 32 may be disposed within the device 200 such that certain freedom of movement (adjustment ability) of the tongue deviating paddle 32 within the device 200 is ensured. Ball joints 19 or 21 which are included in the struts 14 and 16, respectively, and similar structures 34 in tongue deviating paddle 32, or 42B and 44B in the tongue-depressing paddle 40, may be configured to allow a desired range of motion of a protective element (e.g. tongue paddles 32R, 32L, or 40) relative to the dental arch assembly 60. Such ball joints may be secured to their respective struts or paddles. In an embodiment, such assembly and fixation goal may be accomplished using a bonding agent, such as a curable bonding compound (e.g., a cyanoacrylate composition) once a tongue paddle (e.g., paddle 32L, 32R, or 40) is positioned in a desired location. For example, the tongue-deviating paddle 32 may be coupled through the mount 34 with the rod 22 disposed through the strut 14. The front end 32A of the tongue-deviating paddle 32 may be connected with the midline rod 30A disposed through the anterior strut 26. The described structure allows for movement at the front end 32A of tongue-deviating paddle 32 when the midline rod 30A is moved. The excess part of a midline rod 30A may be removed (e.g., cut off or snapped off at broken line 51) once the tongue-deviating paddle (e.g. 32) is secured in a desired position, to provide a new second end 30A3 of midline rod 30A.

Similarly, in an intra-oral device 300 using a tongue-depressing paddle 40, any excess part of a midline rod 30 may be removed (e.g., cut off or snapped off at broken line 51) once the tongue-depressing paddle (e.g. 40) is secured in a desired position, to provide a new second end 303 of midline rod 30.

As shown in FIG. 2, and further described below, the tongue-deviating paddle 32 may be disposed generally vertically relative to the intermaxillary supporting dental arch assembly 60. While in this FIG. 2 the tongue-deviating paddle 32 illustrated is configured to provide a tongue deviation to the left (relative to the patient), a "right hand" version of a tongue-deviating paddle 32R may be configured and mounted similarly to that of the "left hand" version 32L. In an embodiment, the upper dental arch member 10 and/or lower dental arch member 12 may be configured to provide independent support for a protective element such as tongue-deviating paddle 32R or 32L or tongue-depressing paddle 40. For example, a tongue-deviating paddle 32 may be attached to a middle section (somewhere about the center of the U-shape) of the upper dental arch member 10 or to a middle section (somewhere about the center of the U-shape) of the lower dental arch member 12.

Improved versions of the tongue-deviating paddle are shown in FIGS. 17A-17D (132R for movement of the tongue to the right) and 18A-18D (132L for movement of the tongue to the left). Such a tongue-deviating paddle 132R or 132L may be disposed in a roughly vertical configuration, such as depicted in FIGS. 1 and 2. However, note that the tongue-deviating paddles need not be oriented roughly vertically, and may be rotated to any desired angle. As noted in FIG. 1, and elsewhere herein, a tongue-deviating paddle noted with reference numeral 132R may be configured for urging a tongue to a patient's right. For example, as noted in FIG. 2 and elsewhere herein, a tongue-deviating paddle noted with reference numeral 132L may be configured for urging a tongue to a patient's left. In an embodiment, one of the uses of a tongue-deviating paddle, whether 132R or 132L, is to move a patient's tongue away from a side of the patient's mouth that has a cancer to be treated by radiation. Various embodiments for an intra-oral device 100 or 200 may be configured such that the position of a tongue-deviating paddle 132R or 132L may be adjusted to allow for customizing the device 100 or 200 to the particular size and shape of the mouth and tongue of a particular patient.

As seen in FIGS. 17A through 17D, a tongue-depressing paddle 132R may be provided with a tongue protection element 141. Such tongue protection element 141 may be provided in a generally oval-shape, or with a rounded triangular shape, or with a trapezoidal-shape, as suitable in particular circumstances. In an embodiment, joints or concave depressions 142 and/or 144 may be provided, and mounted on a first or mounting side 143 of the paddle 132R. The joints 142 and/or 144 may be provided as concave depressions formed through the surface 143 of the paddle body 141 so that the support struts 126 generally such as shown and described in FIGS. 16A-16G above, and the ball joints 134 specifically, are provided with spherical freedom of movement within joints 142 and/or 144. The joints 142, 144 may be spaced along the length of the paddle body 141 so as to accommodate mouths of different sides and depths and to give some range of motion with spacing preferred between 0 and 2 cm between centers of the depressions.

As seen in FIGS. 18A through 18D, and as with the right-version of the tongue-pressing paddle 132R, a left tongue-depressing paddle 132L may be provided with a tongue protection element 141. Such tongue protection element 141 may be provided in a generally oval-shape, or with a rounded triangular shape, or with a trapezoidal-shape, as suitable in particular circumstances. In an embodiment, joints or concave depressions 142 and/or 144 may be provided, and mounted on a first or mounting side 143 of the paddle 132L. The joints 142 and/or 144 may be provided as concave depressions formed through the surface 143 of the paddle body 141 so that the support struts 126 generally such as shown and described in FIGS. 16A-16G above, and the ball joints 134 specifically, are provided with spherical freedom of movement within joints 142 and/or 144. The joints 142, 144 may be spaced along the length of the paddle body 141 so as to accommodate mouths of different sides and depths and to give some range of motion with spacing preferred between 0 and 2 cm between centers of the depressions.

For both right and left tongue-pressing paddles 132R and 132L, a midline rod 130 couples to a proximal portion of the tongue protection element body 141 and includes a groove 131 formed therein that passes along the length of the rod 130. This groove 131 inserts within a complementary groove formed within the interior surface of the midline ball joint 127 to better lock in the deviation angle of the paddle and prevent slippage.

Figure 19A:
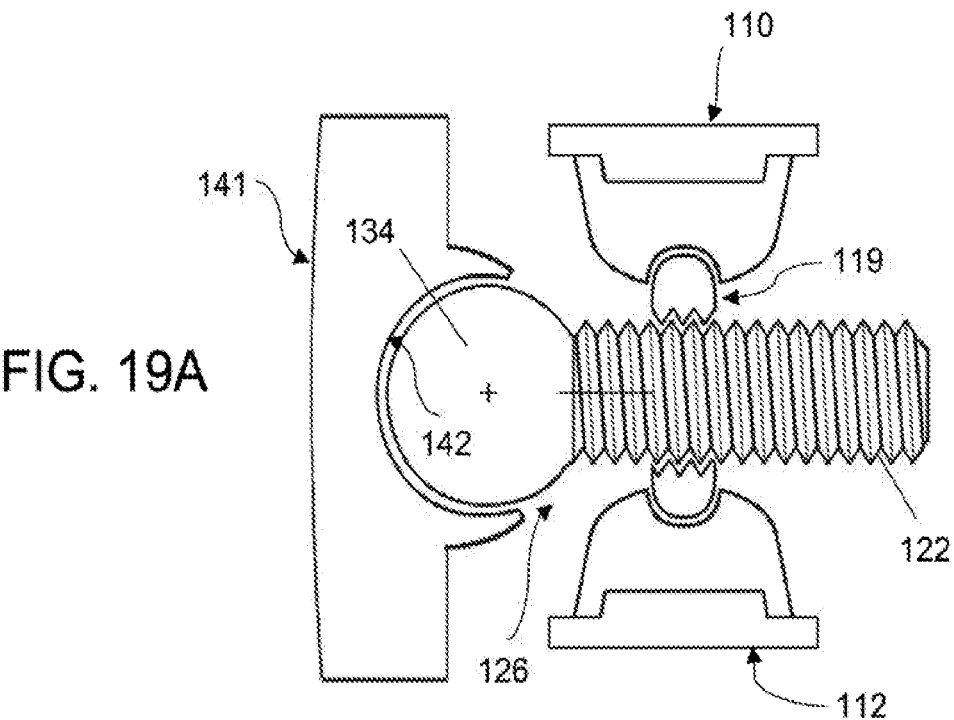
FIGS. 19A-B show partial-sections of side elevation views of the strut threadedly engaged with gimbal in an intermediate and extended position, respectively.
Figure 19B:
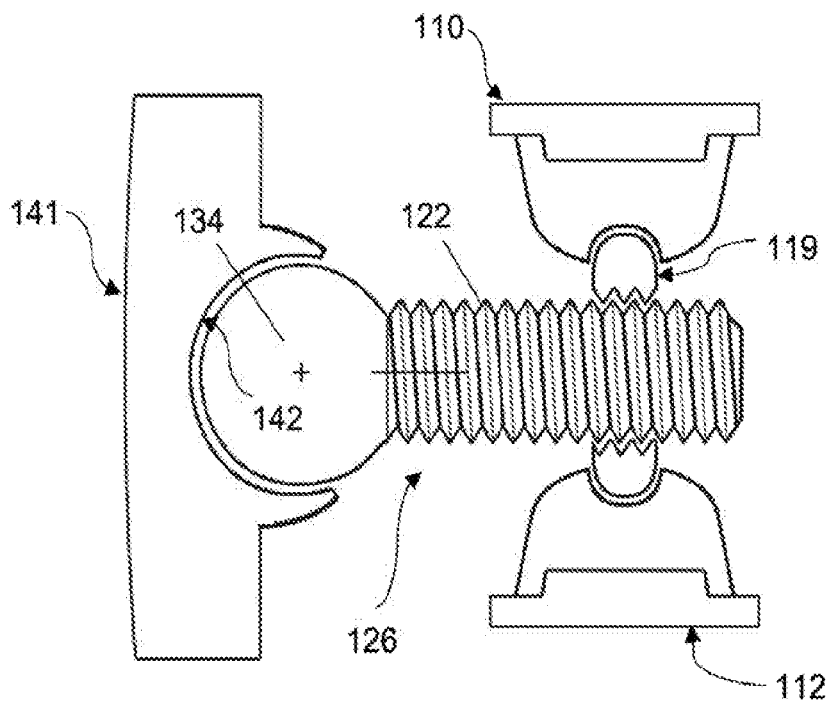

FIGS. 19A and 19B illustrate the adjustable engagement between the paddle 132R and gimbal 119 via an improved threaded strut 126. The male-threaded rod portion 122 of the strut 126 is threaded into the female-threaded portion of gimbal 119 at the desired distance.

FIG. 19A illustrates a small deviation of the paddle body 141 where the supporting strut 126 is threaded to a point along the rod 122 close to the ball-joint head 134. FIG. 19B, in contrast, illustrates a large deviation of the paddle body where the supporting strut 126 is threaded within the gimbal 119 to a point along rod 122 further way from the ball-joint head 134. At the position noted in FIG. 19B, the padded body 141 moves the tongue further to the left side of the mouth than the position shown in FIG. 19A. The gimbal 119 is captured between the upper and lower arches 110, 112 [FIGS. 20A-20B and 21A-21B] similar to the way strut 14 is sandwiched between arches 10 and 12 in FIG. 4. Once the strut 126 is hand-threaded into gimbal 119 the desired distance, the ball-joint end 134 of strut 122 then is snapped into the concave depression 142 formed in the paddle body 141 so that the strut 122 is freely and rotationally moveable within the mounting surface 142.

Turning again to FIG. 3, an embodiment of an intra-oral device 300 will now be further described. FIG. 3 illustrates an example assembly for an intra-oral device 300 that includes a tongue-depressing paddle 40. Similar to the tongue-deviating paddles 32, the tongue-depressing paddle 40 may utilize a midline rod 30 that fits through a ball joint 27 of an anterior strut 26. In an embodiment, a tongue-depressing paddle 40 may be generally a rounded triangular, trapezoidal or oval-shaped and may be positioned generally horizontally as shown in FIG. 3. Like the tongue-deviating paddles 32 described above, a tongue-depressing paddle 40 may be loosely fitted intra-orally into the dental arch assembly 60 (formed by the upper dental arch member 10 and lower dental arch member 12), and positioned using the midline rod 30. Once the tongue-depressing paddle 40 is in a selected position, the tongue-depressing paddle 40 may be immobilized and thus fixed in place via midline rod 30 and anterior strut 26. Then, the midline rod 30 may be shortened as desired. Also, posterior stabilizing rods 22 and 24 may be added for additional strength, and secured to the dental arch assembly 60 and to the tongue-depressing paddle 40. Suitable locking mechanisms or curable bonding agents or the like as mentioned elsewhere herein may be utilized as appropriate to secure and ensure the intended service of the intra-oral device.

Turning again to FIGS. 1 and 2, in an intra-oral device 100 or 200 as set out in such drawing figures, respectively, the upper dental arch member 10 defines an upper plane 90 approximating a plane along the occlusal surfaces 92 of a patent's maxillary teeth 50 or edentulous arch. In various embodiments, as may be understood by additional reference to FIG. 8, a protective element PE, including protective portion PP (e.g., tongue-deviating paddle 32R or 32L) and connector portion CP (e.g., midline rod 30 or 30A) may be deployed in a configuration roughly perpendicular to the upper plane 90. In various embodiments, such roughly perpendicular configuration will vary, anywhere from a precisely perpendicular orientation at ninety (90) degrees to upper plane 90, up to as much of an offset as plus or minus forty five (45) degrees from a perpendicular orientation.

Turning to FIG. 1 for orientation with respect to dental arch member 60, and to FIGS. 3, 4, and 7 as regards an intra-oral device 300, the lower dental arch member 12 defines a lower plane 94 (see FIG. 1) approximating a plane along the occlusal surfaces 96 of a patent's mandibular teeth 50 or edentulous arch. In various embodiments, as may be understood by additional reference to FIG. 4, a protective element PE, including protective portion PP (e.g., tongue-depressing paddle 40) and connector portion CP (e.g., midline rod 30A) may be deployed in a configuration with protective portion PP oriented roughly parallel to the lower plane 90. In various embodiments, such roughly parallel configuration will vary, anywhere from a precisely parallel orientation to lower plane 94, in many embodiments, up to as much of a downward or upward angle (using connector portion CP such as midline rod 30A for evaluation of the angle) of plus or minus forty five (45) degrees from a parallel orientation. In an embodiments for an intra-oral device 300 utilizing a tongue-depressing paddle 40, first posterior stabilizing rod 22 and second posterior stabilizing rod 24 may be structured in an anhedral configuration, where the rods 22 and 24 are extending upward from their respective guides G at struts 14 and 16 toward tongue-depressing paddle 40. In an embodiments for an intra-oral device 300 utilizing a tongue-depressing paddle 40, first posterior stabilizing rod 22 and second posterior stabilizing rod 24 may be structured in a dihedral configuration, where the rods 22 and 24 are extending downward from their respective guides G at struts 14 and 16 toward tongue-depressing paddle 40. In an embodiments for an intra-oral device 300 utilizing a tongue-depressing paddle 40, first posterior stabilizing rod 22 and second posterior stabilizing rod 24 may be structured in a neutral configuration, where the rods 22 and 24 extending substantially horizontally from their respective guides G at struts 14 and 16 toward tongue-depressing paddle 40.

Any of the dental arch assemblies 60, and other components used in intra-oral devices 100, 200 or 300 may be customized for a particular patient. Similarly, the shape of a tongue paddle (e.g. paddles 32L, 32R, or 40) may be adjusted (by material removal, or/and by material addition) to optimize the particular shape of the device to fit a patient's tongue or their other oral tissue limitations (surgical scars, for example) for comfort and/or ideal management. In operation, when the customized device is inserted into the patient's mouth, the tongue paddle (e.g. paddles 32 or 40) will shift the location of a patient's tongue so as to either avoid or reduce adverse effects of head and neck cancer radiation treatment, thus protecting or stabilizing the tongue tissues. The materials selected may optimally be capable of withstanding several weeks of daily high-dose radiation exposure. In an embodiment, an intra-oral device 100, 200 or 300 may be manufactured of a radiation resistant material (thus, in an embodiment, having low radiation absorption and scatter. Accordingly, an intra-oral device 100, 200 or 300 may be manufactured using any suitable material, for example plastics, acrylics, carbon fibers, or other materials having properties consistent with applicable requirements, including various governmental regulations for medical treatment devices used in oral service in humans.

The fill-in material 11F and 13F for the upper member 10 and lower member 12 as described above in reference to FIG. 13A, may include a suitable material having a moldable property. For example, the fill-in material may be made of a customizable material such as Triad® acrylic, a polyether, or polyvinylsiloxane, or other functionally similar materials. When the device 200 or 300 is inserted into the patient's mouth, the patient "molds" the surfaces 10M on the upper member 10, and 12M on the lower member 12, by biting into the fill-in material, which in an embodiment, may be subsequently hardened, for example either autocatalytically or via application of a bright photoactivating light. In this manner, the surfaces 10M and 12M replicate the occlusal surfaces of a particular patient's maxillary teeth 50 and mandibular teeth 52 or comparable edentulous arch forms. The devices 200 or 300 may also be customized, such as by addition of light-cured acrylic to add devices such as lead-lined lip bumpers, cheek bumpers near metallic crowns, and the like.

FIGS. 20A and 20B illustrate an improved version of upper dental arch 10 described above. The improved upper dental arch member 110 may be separately provided in a kit 400 (e.g., see FIG. 14), whereby a selection of upper dental arch members 110 may be provided in preselected sizes, having a configuration complementary in size and shape to that of maxillary dental arch dimensions found in a selected group of anticipated patients. In an embodiment, an upper dental arch member 110 may be provided in a generally U-shaped (e.g., horseshoe shaped) configuration. An upper dental arch member 110 may be provided in various sizes, such as small, medium, large, or other sizes. Such arch member 110 is preferably formed of injection-molded polycarbonate and/or Lexan HPS1.

As may be appreciated from FIGS. 2, 3, 4 and 13A, in an embodiment, an upper dental arch member 110 may have an upper side 110U. An upwardly directed upper receiving trough 111 may be disposed on or in the upper side 110U. As seen in FIG. 13A, the upper receiving trough 111 may be adapted to receive a fill-in material 11F, which fill-in material 11F may be molded to customize the fit of the upper dental arch member 110 to an individual patient's maxillary teeth 50 (see FIG. 1) or edentulous maxillary arch. The upper receiving trough may be variously adapted to receive a moldable compound for fabrication into a bite pad for secure receipt of the occlusal surface of a patient's maxillary teeth or edentulous arch.

Retention of the bite pad (e.g. element 10M shown in FIG. 13A) within the trough 111 is preferably accomplished by way of keyways or apertures formed through the trough side and/or bottom surface. The trough 111 of the improved upper dental arch member 110 includes an array of keyway apertures, such as apertures 113, that pass from and through the upper side 110U to the lower side 110L of upper dental arch member 110. A moldable compound such as described above is placed within the trough 111 and heated up as by soaking the assembly in hot water (e.g. around 85-95° C.) for between about 30 and 60 seconds. The assembly is then placed in a patient's mouth and the patient bites down onto the moldable compound material for 15 seconds to form teeth impressions. The pressure of the patient's bite not only forms the teeth impression 10M on the top surface of the moldable compound, but also forces a portion of the moldable material through the keyway apertures 113 (see, e.g. FIG. 13A). Depending upon the current state and viscosity of the moldable compound, the materials can completely fill the passageway 113 between the top and bottom surfaces of the dental arch and/or mushroom out the opposite side to help lock the moldable material in place within the trough 111. The assembly is then rinsed in cold water to set the impression as well as the extruded portions 115 that flowed through the keyway apertures 113.

The improved upper dental arch member 110 is also formed with pins or pegs 117 that extend out the lower side 110L. These pegs 117 are positioned on the underside of arch member 110 in a pattern that matches complementary structures formed on the lower dental arch member. As shown in FIG. 21A, these complementary structures take the form of channels or apertures 121 that receive respective pins 117 within and lock and align the upper dental arch 110 to the lower dental arch 112. Preferred embodiments of the upper dental arch 110 include a pair of pins 117 on each rear portion of the arch and a set of three pins arranged in an asymmetric pattern at the front of the arch. When the upper dental arch member 110 is locked together with the lower dental arch member 112, as via pins 117 and apertures 121, the combined intra-oral device define annular grooves 123, 125 into which the gimble 119 and ball joint 127 are installed, respectively.

FIGS. 21A and 21B illustrate an improved version of lower dental arch 12 described above. The improved lower dental arch member 112 may be separately provided in a kit 400 (e.g., see FIG. 14), whereby a selection of lower dental arch members 112 may be provided in preselected sizes, having a configuration complementary in size and shape to that of maxillary dental arch dimensions found in a selected group of anticipated patients. In an embodiment, an lower dental arch member 112 may be provided in a generally U-shaped (e.g., horseshoe shaped) configuration. An lower dental arch member 112 may be provided in various sizes, such as small, medium, large, or other sizes.

As may be appreciated from FIGS. 2, 3, 4 and 13A, in an embodiment, a lower dental arch member 112 may have an upper side 112U. An upwardly directed upper receiving trough 111 may be disposed on or in the upper side 112U. As seen in FIG. 13B, the upper receiving trough 111 may be adapted to receive a fill-in material 12F, which fill-in material 12F may be molded to customize the fit of the lower dental arch member 112 to an individual patient's maxillary teeth 50 (see FIG. 1) or edentulous maxillary arch. The lower receiving trough may be variously adapted to receive a moldable compound for fabrication into a bite pad for secure receipt of the occlusal surface of a patient's maxillary teeth or edentulous arch.

Retention of the bite pad (e.g. element 10M shown in FIG. 13A) within the trough 111 is preferably accomplished by way of keyways or apertures formed through the trough side and/or bottom surface as noted above with respect to the upper dental arch bite pad. That is, the trough 111 of the improved lower dental arch member 112 includes an array of keyway apertures, such as apertures 113, that pass from and through the upper side 112U to the lower side 112L of lower dental arch member 112. A moldable compound such as described above is placed within the trough 111 and heated up as by soaking the assembly in warm or hot water (e.g. around 80° C.) for between about 30 and 60 seconds. The assembly is then placed in a patient's mouth and the patient bites down onto the moldable compound material for 15 seconds to form teeth impressions. The pressure of the patient's bite not only forms the teeth impression 12M on the top surface of the moldable compound, but also forces a portion of the moldable material through the keyway apertures 113 (see, e.g. FIG. 13B). Depending upon the current state and viscosity of the moldable compound, the materials can completely fill the passageway 113 between the top and bottom surfaces of the dental arch and/or mushroom out the opposite side to help lock the moldable material in place within the trough 111. The assembly is then rinsed in cold water to set the impression as well as the extruded portions 115 that flowed through the keyway apertures 113.

It is preferred that the upper and lower dental arches be press-fit together as by the pins 117 and holes 121 described above and the moldable materials placed in the troughs 111 of both the upper and lower dental arches 110, 112. The patient may then bite down on both arches and form the molded impressions 10M and 12M at the same time while also forcing a portion of the moldable material through keyways 113 to help lock the moldable material within the dental arch troughs 111. Molded annular arches formed on the lower sides 110L and 112L at the back end of each arch receive a gimbal 119 for movement within.

In the foregoing description, numerous details have been set forth in order to provide a thorough understanding of the disclosed exemplary embodiments for an intra-oral device for positioning certain oral tissue during radiation treatment. The purpose of the intra-oral devices described here is to provide a wide range of flexibility to give the end user of the device as much latitude to customize and idealize its application for the maximum benefit of the patient. However, certain of the described details may not be required in order to provide useful embodiments, or to practice selected or other disclosed embodiments. Further, the description may include, for descriptive purposes, various relative terms such as surface, at, adjacent, proximity, near, on, onto, and the like. Such usage should not be construed as limiting. Terms that are relative only to a point of reference are not meant to be interpreted as absolute limitations, but are instead included in the foregoing description to facilitate understanding of the various aspects of the disclosed embodiments. Various components are described which may be employed alternatively, yet be included in a kit or product package to enable an end user to select the optimal components for use in a particular situation. Accordingly, procedures utilizing the intra-oral device described herein, and the method(s) described herein may be utilized as multiple discrete operations, in a manner that is most helpful in a particular circumstance. However, the order of description should not be construed as to imply that such alternatives are necessarily order dependent, or that use of various components is necessarily in the alternative. Also, the reader will note that the phrase "in one embodiment" has been used repeatedly. This phrase generally does not refer to the same embodiment; however, it may. Finally, the terms "comprising", "having" and "including" should be considered synonymous, unless the context dictates otherwise.

Various aspects and embodiments described and claimed herein may be modified from those shown without materially departing from the novel teachings and advantages provided by this invention, and may be embodied in other specific forms without departing from the spirit or essential characteristics thereof. Embodiments presented herein are to be considered in all respects as illustrative and not restrictive or limiting. This disclosure is intended to cover methods and apparatus described herein, and not only structural equivalents thereof, but also equivalent structures. Modifications and variations are possible in light of the above teachings. Therefore, the protection afforded to this invention should be limited only by the claims set forth herein, and the legal equivalents thereof.

Having described and illustrated the principles of the invention in a preferred embodiment thereof, it should be apparent that the invention can be modified in arrangement and detail without departing from such principles. I claim all modifications and variation coming within the spirit and scope of the following claims.

What is claimed is:

1. An intra-oral device for positioning oral tissues in a patient with or without maxillary and/or mandibular teeth, said device comprising:
    (a) a dental arch assembly, said dental arch assembly comprising
        an upper dental arch member having a first end and a second end, said upper dental arch member configured for engagement with the maxillary teeth or edentulous arch of the patient;
        a lower dental arch member having a third end and a fourth end, the lower dental arch member configured for engagement with the mandibular teeth or edentulous arch of the patient; and complementary structures arranged for press-fitting the upper and lower dental arch together; and (b) a protective element, said protective element comprising a protective portion and a connector portion, said protective element coupled to said dental arch assembly, said protective element configured to engage oral tissues of a patient, wherein said connector portion includes a threaded rod adjustably engageable with a threaded structure disposed between the upper and lower dental arch member and ending with a ball joint captured within a depression formed on a surface of the protective element for rotational movement of the ball joint within the depression.

2. The intra-oral device of claim 1, wherein the complementary structures comprise first structures including pins or pegs projecting from an underside of one of the upper dental arch member or lower dental arch member and second structures including channels or apertures formed on an opposed underside of another of the upper dental arch member or lower dental arch member, wherein said first and second structures are operative to lock and align the upper and lower dental arch members together.

3. The intra-oral device of claim 2, wherein the first structures are arranged in an asymmetric pattern.

4. The intra-oral device of claim 2, wherein the first structures are a pair of pins projecting from each rear portion of the upper dental arch and a set of three pins arranged in an asymmetric pattern at a front of the upper dental arch member.

5. The intra-oral device of claim 1, wherein said protective element comprises a tongue-deviating paddle coupled to a proximal portion of the intra-oral device and to an inside-right or inside-left side of the intra-oral device and operative to push a tongue of the patient laterally right or left, respectively.

6. The intra-oral device of claim 5, wherein the connector portion includes a midline rod coupled on one end to a proximal end of the tongue-deviating paddle and on another end to a midline ball joint interposed between the upper and lower dental arch members of the intra-oral device.

7. The intra-oral device of claim 6, wherein the midline rod has a groove passing along a length of the midline rod that is configured to engage with a complementary groove formed within an interior surface of the midline ball joint so that the tongue-deviating paddle is aligned in an upright fashion sufficient to properly contact the tongue of the patient.

8. The intra-oral device of claim 5, wherein the protective portion comprises a working side adapted to contact the tongue of the patient and an opposed side having a plurality of concave depressions configured to receive the ball joint of the connector portion.

9. The intra-oral device of claim 1, wherein the threaded structure disposed between the upper and lower dental arch members is a gimbal.

10. The intra-oral device of claim 9, wherein the threaded rod includes a plurality of slots formed along a length of the rod configured to allow the rod to compress and effect a greater friction fit within the gimbal when received therein.

11. The intra-oral device of claim 1, wherein the threaded rod is partially threaded along its length.

12. An intra-oral device as set forth in claim 1, wherein said upper dental arch member further comprises an upper receiving trough with keyways formed therethrough, said upper receiving trough and keyways adapted to receive a moldable compound for fabrication into a bite pad for secure receipt of an occlusal surface of the patient's maxillary teeth or edentulous arch.

13. An intra-oral device as set forth in claim 1, wherein said lower dental arch member further comprises a lower receiving trough with keyways formed therethrough, said lower receiving trough and keyways adapted to receive a moldable compound for fabrication into a bite pad for receipt of an occlusal surface of the patient's mandibular teeth or edentulous arch.

14. The intra-oral device as set forth in claim 1, wherein at least one of said upper and/or lower dental arch member further comprises a receiving trough with keyways formed therethrough, said receiving trough and keyways adapted to receive a moldable compound for fabrication into a bite pad for secure receipt of an occlusal surface of the patient's maxillary teeth or edentulous arch, wherein said trough has a wedge-shaped profile such that an inner portion is shallower than an outer portion.

* * * * *